United States Patent
Tiwari et al.

(10) Patent No.: US 10,921,408 B2
(45) Date of Patent: Feb. 16, 2021

(54) PROBABILISTIC ATLASES OF POST-TREATMENT MULTI-PARAMETRIC MRI SCANS REVEAL DISTINCT HEMISPHERIC DISTRIBUTION OF GLIOBLASTOMA PROGRESSION VERSUS PSEUDO-PROGRESSION

(71) Applicant: Case Western Reserve University, Cleveland, OH (US)

(72) Inventors: Pallavi Tiwari, Wexford, PA (US); Marwa Ismail, Louisville, KY (US); Anant Madabhushi, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 35 days.

(21) Appl. No.: 16/507,559

(22) Filed: Jul. 10, 2019

(65) Prior Publication Data

US 2020/0081085 A1    Mar. 12, 2020

Related U.S. Application Data

(60) Provisional application No. 62/730,108, filed on Sep. 12, 2018.

(51) Int. Cl.
| | |
|---|---|
| *G06T 7/33* | (2017.01) |
| *G01R 33/56* | (2006.01) |
| *G06F 17/18* | (2006.01) |
| *G16H 20/40* | (2018.01) |
| *G06T 7/10* | (2017.01) |
| *G16H 20/10* | (2018.01) |
| *G16H 30/40* | (2018.01) |

(52) U.S. Cl.
CPC ............ *G01R 33/56* (2013.01); *G06F 17/18* (2013.01); *G06T 7/10* (2017.01); *G06T 7/337* (2017.01); *G16H 20/10* (2018.01); *G16H 20/40* (2018.01); *G16H 30/40* (2018.01); *G06T 2207/10088* (2013.01); *G06T 2207/30016* (2013.01); *G06T 2207/30096* (2013.01)

(58) Field of Classification Search
None
See application file for complete search history.

(56) References Cited

U.S. PATENT DOCUMENTS 9,662,039 B2 *  5/2017  Liu ...................... A61B 5/055

* cited by examiner

*Primary Examiner* — Matthew C Bella
*Assistant Examiner* — Brian D Shin
(74) *Attorney, Agent, or Firm* — Eschweiler & Potashnik, LLC

(57) ABSTRACT

Embodiments discussed herein facilitate generating a quantitative population atlas of tumor progression (TP) versus pseudo-progression (PsP) in Glioblastoma (GBM). A first set of embodiments discussed herein relates to generating a quantitative population atlas of TP versus PsP based on a plurality of multi-parametric (mpMRI) studies of a population of patients demonstrating GBM. A second set of embodiments discussed herein relates to computing a probability that a patient will experience PsP or TP based on a DICE analysis of a mapping of a diagnostic mpMRI study associated with the patient into the quantitative population atlas space.

19 Claims, 14 Drawing Sheets

| Characteristic | Population cohort |
| --- | --- |
| No. of patients | 105 |
| Women | 36 |
| Men | 69 |
| Mean age (year) | 58.1 |
| Age range (year) | 25 – 76 |

710

|  | Tumor Progression | PsP | |
|---|---|---|---|
| Lesion positive | $a$ | $c$ | $a + c$ |
| Lesion negative | $b$ | $d$ | $b + d$ |
|  | $a + b$ | $c + d$ | $n$ |

810

PROBABILISTIC ATLASES OF POST-TREATMENT MULTI-PARAMETRIC MRI SCANS REVEAL DISTINCT HEMISPHERIC DISTRIBUTION OF GLIOBLASTOMA PROGRESSION VERSUS PSEUDO-PROGRESSION

CROSS REFERENCE TO RELATED APPLICATIONS

This application claims the benefit of U.S. Provisional Patent Application No. 62/730,108 filed Sep. 12, 2018, entitled "PROBABILISTIC ATLASES OF POST-TREATMENT MULTI-PARAMETRIC MRI SCANS REVEAL DISTINCT HEMISPHERIC DISTRIBUTION OF GLIOBLASTOMA PROGRESSION VERSUS PSEUDO-PROGRESSION", the contents of which are herein incorporated by reference in their entirety.

FEDERAL FUNDING NOTICE

This invention was made with government support under the grant(s) W81XWH-18-1-0404 awarded by the Department of Defense. The government has certain rights in the invention.

BACKGROUND

A significant challenge in post-treatment assessment of Glioblastoma (GBM) differentiating tumor recurrence or tumor progression (TP) from pseudo-progression (PsP), a radiation-induced treatment effect, on routine magnetic resonance imaging (MRI) scans. Studies on pre-treatment MRI suggest that aggressive GBM lesions are spatially localized in the right hemisphere, and are associated with poor survival. Aggressive TP lesions appearing on post-treatment scans may be more localized in the right hemisphere, as compared to benign PsP.

PsP is a benign radiation-induced treatment effect which occurs in approximately 19% to 33% of all malignant brain tumors and usually stabilizes or regresses without further treatment. Unfortunately, PsP mimics tumor progression radiologically on routine MRI scans (Gadolinium-enhanced T1-weighted (Gd-$T_{1w}$), T2-weighted ($T_{2w}$), FLAIR), making it challenging to differentiate from true tumor recurrence or tumor progression. Existing approaches employ advanced imaging modalities such as perfusion imaging, MR spectroscopy, and diffusion-weighted imaging in distinguishing tumor progression from PsP. However, results of these existing approaches are not easily reproduced. Reliable imaging biomarkers are thus needed in order to aid in accurately identifying PsP from TP.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

DETAILED DESCRIPTION

Figure 1:
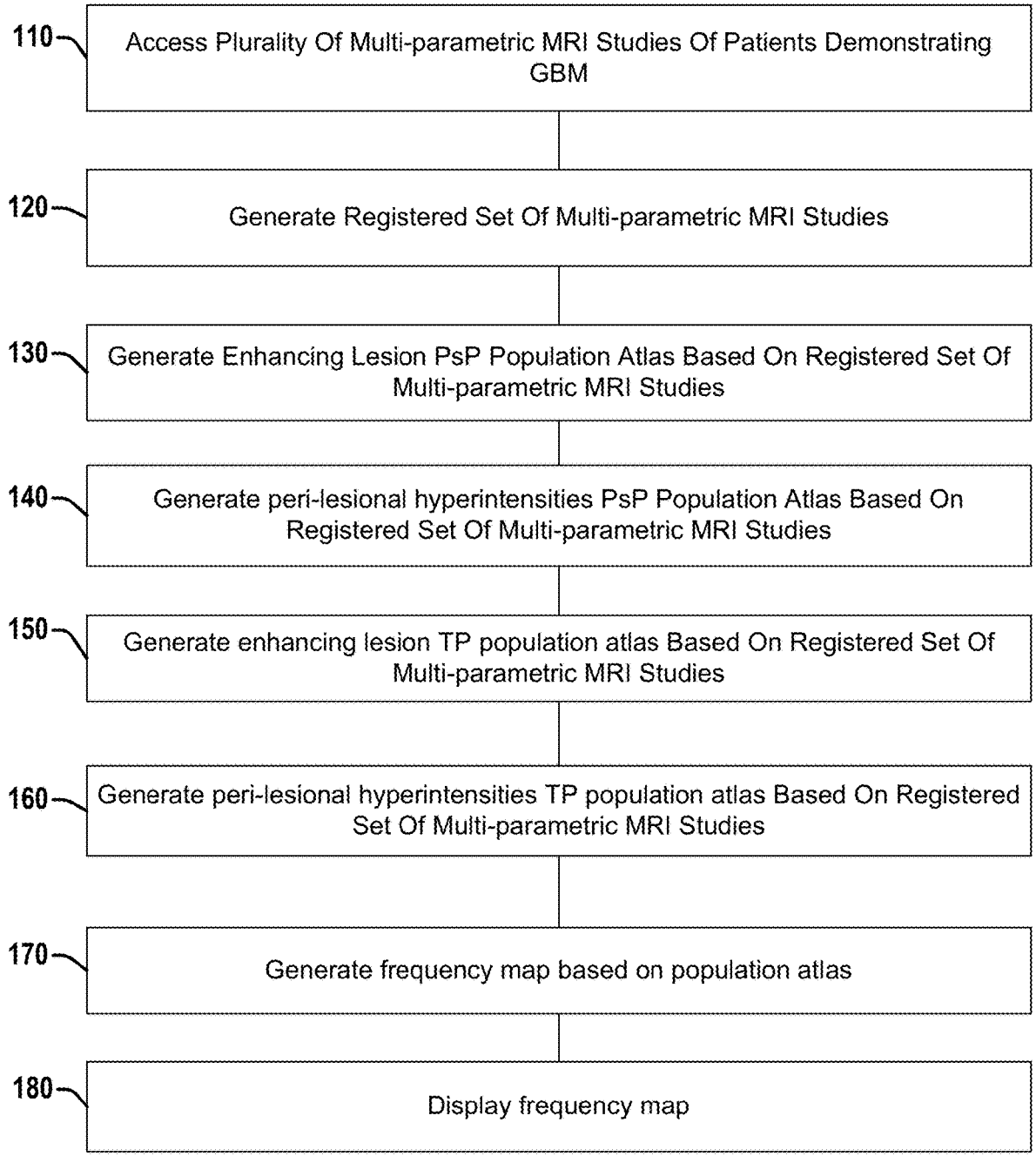
FIG. 1 illustrates a diagram of a first example flow of a method or set of operations that generates a quantitative population atlas of tumor progression (TP) versus pseudo-progression (PsP), according to various embodiments discussed herein.

Tumor recurrence or tumor progression (TP) tends to be lateralized towards the right parietal lobe. Pseudo-progression PsP tends to be multi-focally distributed in the left hemisphere. Embodiments described herein improve on existing approaches to differentiating PsP from TP in patients demonstrating GBM by employing such spatial localization on MRI to serve as a biomarker for differentiating PsP and TR Embodiments facilitate providing more immediate treatment changes in patients with recurrence, while avoiding unnecessary treatment for PsP, compared to existing approaches. Embodiments create and employ quantitative population atlases of TP versus PsP to facilitate differentiation of PsP from TP using spatial predisposition of PsP or TP to specific locations in the brain, based on their occurrences on routine MRI scans, including post-treatment, or pre-treatment, MRI scans.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Various embodiments can employ techniques discussed herein to facilitate generating a quantitative population atlas of TP versus PsP. Referring to FIG. 1, illustrated is a diagram showing a first example flow of a method or set of operations 100 that generates a quantitative population atlas of TP versus PsP, according to various embodiments discussed herein. Operations 100 may comprise acquiring electronic data, reading from a computer file, receiving a computer file, reading from a computer memory, or other computerized activity not practically performed in the human mind.

The set of operations 100 includes, at 110, accessing a plurality of multi-parametric magnetic resonance imaging (mpMRI) studies associated with a plurality of patients demonstrating Glioblastoma (GBM), respectively. The plurality of mpMRI studies may comprise a plurality of mpMRI studies comprising a positive set that is associated with a first classification (e.g., TP) and a negative set that is associated with a different second classification (e.g., PsP). For example, in this embodiment, at least one member of the plurality of mpMRI studies is associated with a patient that demonstrated PsP, and at least one other, different member of the plurality of mpMRI studies is associated with a patient that demonstrated TP. An mpMRI study includes a plurality of MRI images, where a member of the plurality of MRI images includes a plurality of associated voxels, a voxel having an intensity. The accessed plurality of mpMRI studies, or a member of the plurality of MRI images, can be stored in memory locally or remotely, and can be obtained via a medical imaging device one of concurrently with method 100 (e.g., via a medical imaging device implementing method 100) or prior to method 100. A first member of the plurality of MRI images may be acquired according to a first MRI sequence, while a second, different member of the plurality of MRI images may be acquired according to a second, different MRI sequence, while a third, different member of the plurality of MRI images may be acquired by a third, different MRI sequence. For example, in one embodiment, the mpMRI study includes a Gd-T1w MRI image, a T2w MRI image, and a FLAIR MRI image, where the Gd-T1w MRI image, the T2w MRI image, and the FLAIR MRI image each includes a plurality of associated voxels, a voxel having an intensity. While in this embodiment, a Gd-T1w MRI image, a T2w MRI image, and a FLAIR MRI image are described, in another embodiment, other, different MRI sequences may be employed.

Figure 2:
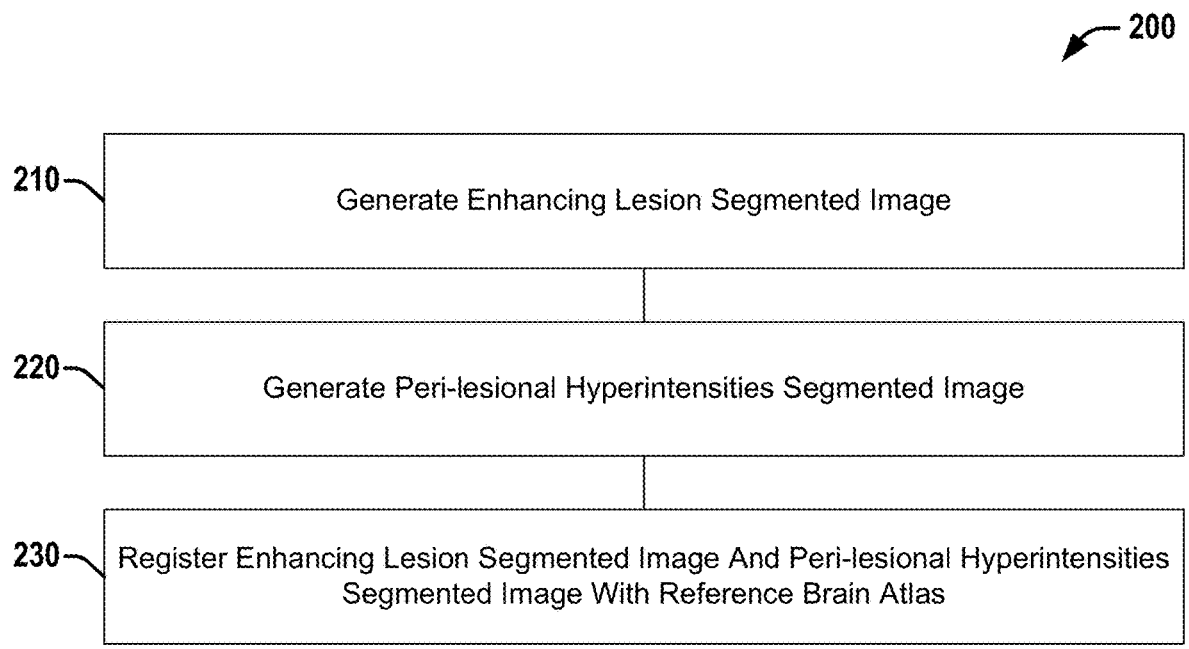
FIG. 2 illustrates a diagram of a first example flow of a method or set of operations that generates a registered set of multi-parametric MRI (mpMRI) studies according to various embodiments discussed herein.

The set of operations 100 also includes, at 120, generating a registered set of mpMRI studies based on the plurality of mpMRI studies. Referring to FIG. 2, illustrated is a diagram of a first example flow of a method or set of operations 200 that facilitate generation of a registered set of mpMRI studies according to various embodiments discussed herein. Operations 200 may comprise acquiring electronic data, reading from a computer file, receiving a computer file, reading from a computer memory, or other computerized activity not practically performed in the human mind. Operations 200 includes, at 210 generating an enhancing lesion segmented image by segmenting an enhancing lesion compartment represented in a first MRI image acquired during a first MRI sequence of a member of the plurality of multi-parametric MRI studies associated with a patient. The first MRI sequence may be, for example, a Gd-T1w MRI sequence.

Operations 200 also includes, at 220, generating a peri-lesional hyperintensities segmented image by segmenting a peri-lesional hyperintensities compartment represented in a second, different MRI image acquired during a second, different MRI sequence of the member of the plurality of multi-parametric MRI studies associated with the patient. The second, different MRI sequence may be, for example, a T2w MRI sequence or a FLAIR MRI sequence.

In one embodiment, generating the enhancing lesion segmented image includes segmenting an enhancing lesion compartment represented in the Gd-T1w MRI image. In this embodiment, generating the peri-lesional hyperintensities segmented image also includes segmenting a peri-lesional hyperintensities compartment represented in the T2w MRI image, and segmenting a peri-lesional hyperintensities compartment represented in the FLAIR MRI image. In various embodiments, automated segmentation techniques may be employed, including for example, DeepMedic brain tumor segmentation, Cancer Imaging Phenomics Toolkit (CaPTk) segmentation, or a radiomics-based convolutional neural network for brain tumor segmentation on multiparametric magnetic resonance imaging (RADCNN) technique.

Figure 3:
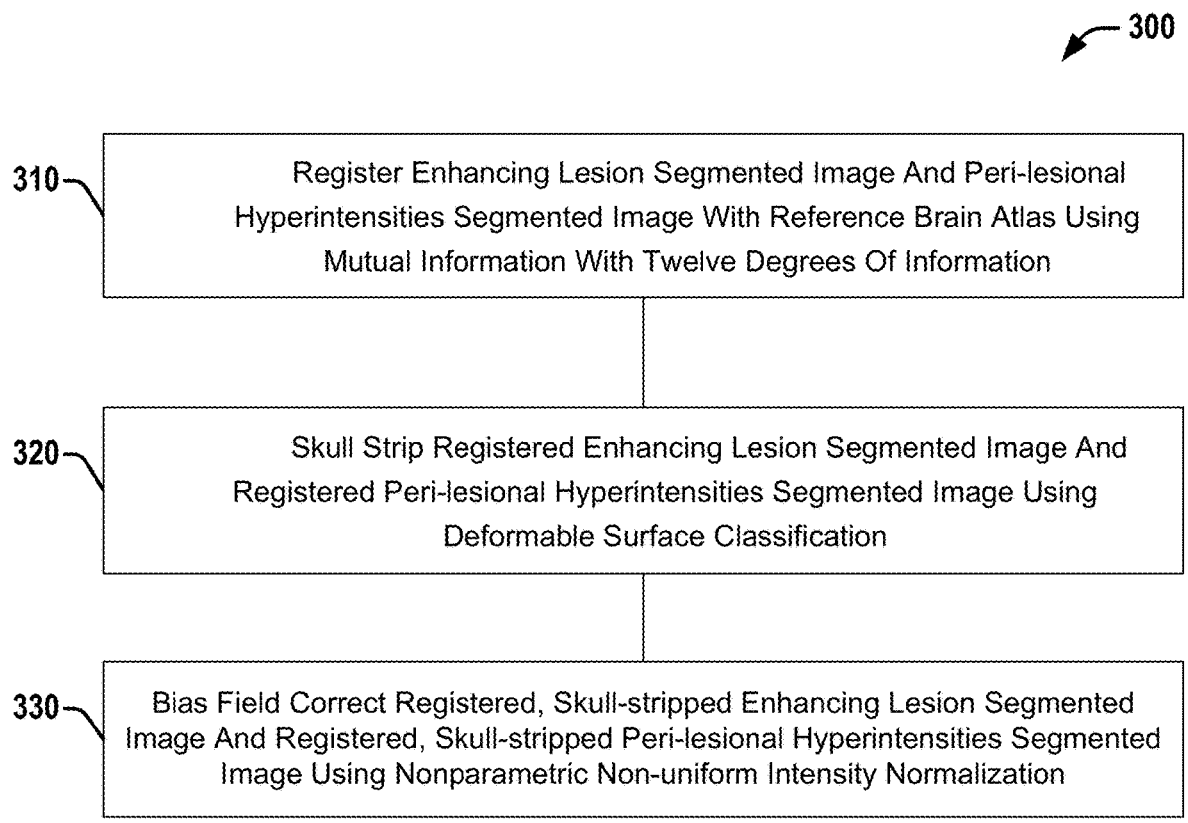
FIG. 3 illustrates a diagram of a first example flow of a method or set of operations that registers an enhancing brain lesion segmented image and a peri-lesional hyperintensities segmented image with a reference brain atlas according to various embodiments discussed herein.

Operations 200 further includes, at 230, registering the enhancing lesion segmented image and the peri-lesional hyperintensities segmented image with a reference brain atlas. The reference brain atlas may be, for example, a Montreal Neurological Institute (MNI) 152 brain atlas. FIG. 3 illustrates a diagram of a first example flow of a method or set of operations 300 that registers an enhancing brain lesion segmented image and a peri-lesional hyperintensities segmented image with a reference brain atlas according to various embodiments discussed herein. Operations 300 may comprise acquiring electronic data, reading from a computer file, receiving a computer file, reading from a computer memory, or other computerized activity not practically performed in the human mind.

Operations 300 includes, at 310, generating a registered enhancing lesion segmented image and a registered peri-lesional hyperintensities segmented image by registering the enhancing lesion segmented image and the peri-lesional hyperintensities segmented image with the reference brain atlas using mutual information with twelve degrees of information. In another embodiment, other registration techniques may be employed.

Operations 300 also includes, at 320, generating a registered, skull-stripped enhancing lesion segmented image and a registered, skull-stripped peri-lesional hyperintensities segmented image by skull stripping the registered enhancing lesion segmented image and the registered peri-lesional hyperintensities segmented image using a deformable surface classification approach. In another embodiment, other skull-stripping techniques may be employed.

Operations 300 further includes, at 330, bias field correcting the registered, skull-stripped enhancing lesion segmented image and the registered, skull-stripped peri-lesional hyperintensities segmented image. In this embodiment, a nonparametric non-uniform intensity normalization technique is employed for bias field correction. In another embodiment, another, different bias field correction technique may be employed.

Returning to FIG. 1, the set of operations 100 also includes, at 130, generating an enhancing lesion PsP population atlas by computing a voxel-wise frequency of occurrence of enhancing lesion of the members of the registered set of mpMRI studies associated with patients who demonstrated PsP. In one embodiment, computing the voxel-wise frequency of occurrence of enhancing lesion of the members of the registered set of mpMRI studies associated with patients who demonstrated PsP includes computing the average intensity value for each voxel of each annotated enhancing lesion image of each mpMRI study associated with patients who demonstrated PsP.

The set of operations 100 also includes, at 140, generating a peri-lesional hyperintensities PsP population atlas by computing a voxel-wise frequency of occurrence of peri-lesional hyperintensities of the members of the registered set of mpMRI studies associated with patients who demonstrated PsP. In one embodiment, computing the voxel-wise frequency of occurrence of peri-lesional hyperintensities of the members of the registered set of mpMRI studies associated with patients who demonstrated PsP includes computing the average intensity value for each voxel of each annotated peri-lesional hyperintensities image of each multiparametric study associated with patients who demonstrated PsP.

The set of operations 100 also includes, at 150, generating an enhancing lesion TP population atlas by computing a voxel-wise frequency of occurrence of enhancing lesion of the members of the registered set of mpMRI studies associated with patients who demonstrated TP. In one embodiment, computing the voxel-wise frequency of occurrence of enhancing lesion of the members of the registered set of mpMRI studies associated with patients who demonstrated TP based on the registered set of mpMRI studies includes computing the average intensity value for each voxel of each annotated enhancing lesion image of each multiparametric study associated with patients who demonstrated TP.

The set of operations 100 also includes, at 160, generating a peri-lesional hyperintensities TP population atlas by computing a voxel-wise frequency of occurrence of peri-lesional hyperintensities of members of the registered set of mpMRI studies who demonstrated TP. In one embodiment, computing the voxel-wise frequency of occurrence of peri-lesional hyperintensities of the members of the registered set of mpMRI studies associated with patients who demonstrated TP based on the registered set of mpMRI studies includes computing the average intensity value for each voxel of each annotated peri-lesional hyperintensities image of each mpMRI study associated with patients who demonstrated TP. While in this embodiment, computing average intensity values for each voxel of the respective members of the registered set of mpMRI studies is described, in another embodiment, average intensity values may be computed for less than each voxel. For example, in one embodiment, average intensity values may be computed for 90%, 80%, or another, different percentage of voxels.

The set of operations 100 also includes, at 170, generating a frequency map for at least one of the enhancing lesion PsP population atlas, the peri-lesional hyperintensities PsP population atlas, the enhancing lesion TP population atlas, or the peri-lesional hyperintensities TP population atlas. In one embodiment, the frequency map is represented as a heat map superimposed on the reference brain atlas. Generating and displaying the frequency map provides a practical integration of at least the population atlases generated according to various embodiments described herein with medical or computer technology employed to differentiate PsP from TP or to manage GBM.

The set of operations 100 further includes, at 180, displaying the frequency map, and can optionally comprise displaying one or more of the enhancing lesion PsP population atlas, the peri-lesional hyperintensities PsP population atlas, the enhancing lesion TP population atlas, or the peri-lesional hyperintensities TP population atlas. Displaying the frequency map can comprise displaying the frequency map and optionally displaying one or more of the enhancing lesion PsP population atlas, the peri-lesional hyperintensities PsP population atlas, the enhancing lesion TP population atlas, or the peri-lesional hyperintensities TP population atlas on a computer monitor, a smartphone display, a tablet display, or other displays. Displaying the frequency map and optionally displaying one or more of the enhancing lesion PsP population atlas, the peri-lesional hyperintensities PsP population atlas, the enhancing lesion TP population atlas, or the peri-lesional hyperintensities TP population atlas can also comprise printing the frequency map and optionally printing one or more of the enhancing lesion PsP population atlas, the peri-lesional hyperintensities PsP population atlas, the enhancing lesion TP population atlas, or the peri-lesional hyperintensities TP population atlas. By displaying the frequency map and optionally displaying one or more of the enhancing lesion PsP population atlas, the peri-lesional hyperintensities PsP population atlas, the enhancing lesion TP population atlas, or the peri-lesional hyperintensities TP population atlas, example embodiments provide a timely and intuitive way for a human medical practitioner to more accurately predict the likelihood a GBM patient will experience PsP or TP, thus improving on existing approaches to predicting PsP or TP.

Embodiments may further display operating parameters of the machine learning classifier.

Figure 4:
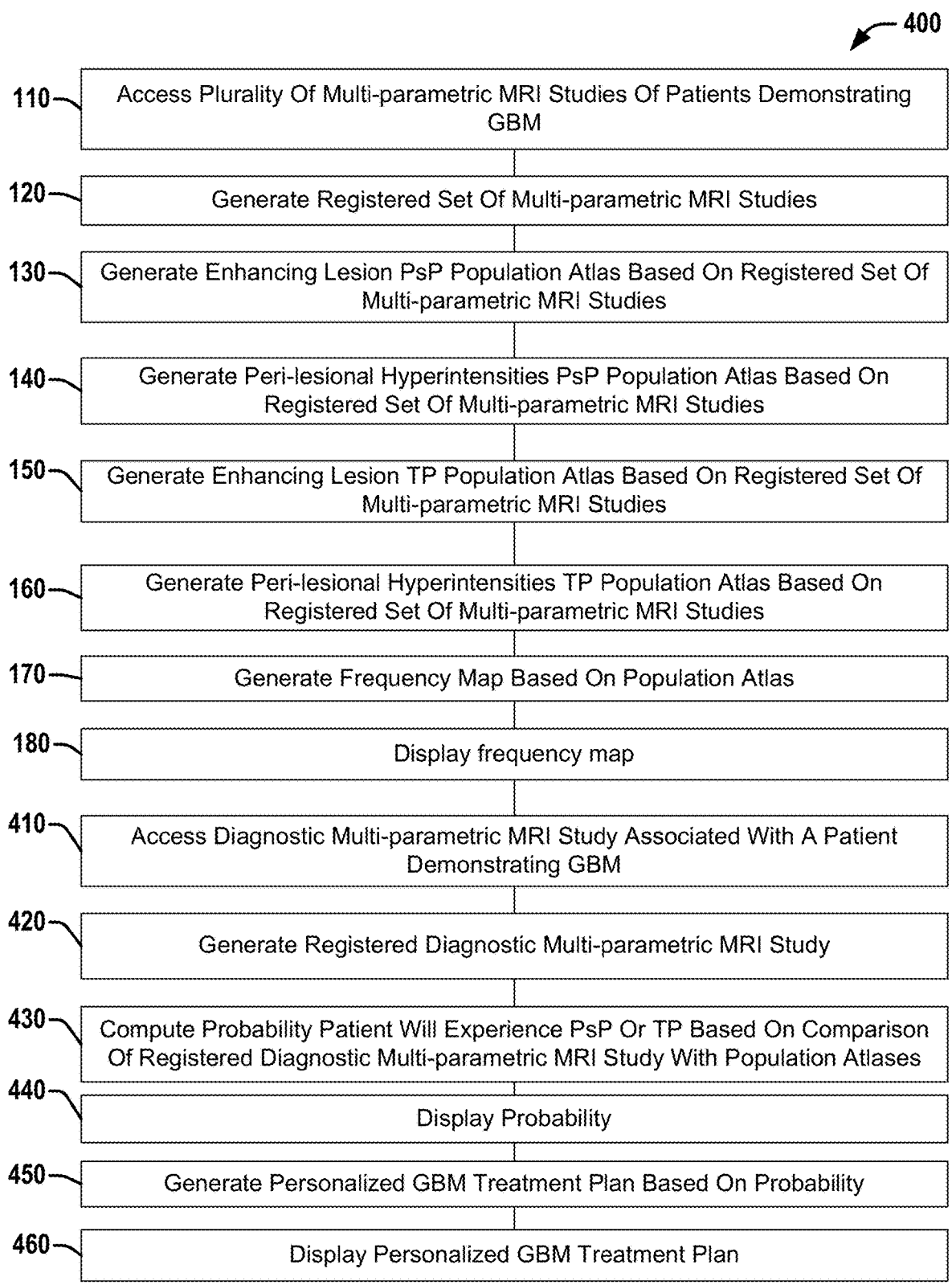
FIG. 4 illustrates a diagram of a second example flow of a method or set of operations that generates a quantitative population atlas of TP versus PsP, according to various embodiments discussed herein.

FIG. 4 illustrates a diagram of a second example flow of a method or set of operations 400 that generate a quantitative population atlas of TP versus PsP, according to various embodiments discussed herein. Operations 400 is similar to operations 100, but includes additional elements and details. Operations 400 includes operations 110-180. Operations 400 also includes, at 410, accessing a diagnostic multi-parametric MRI study associated with a patient demonstrating GBM. The diagnostic multi-parametric MRI study includes a plurality of MRI images. A member of the plurality of MRI images includes a plurality of associated voxels, a voxel having an intensity.

Figure 5:
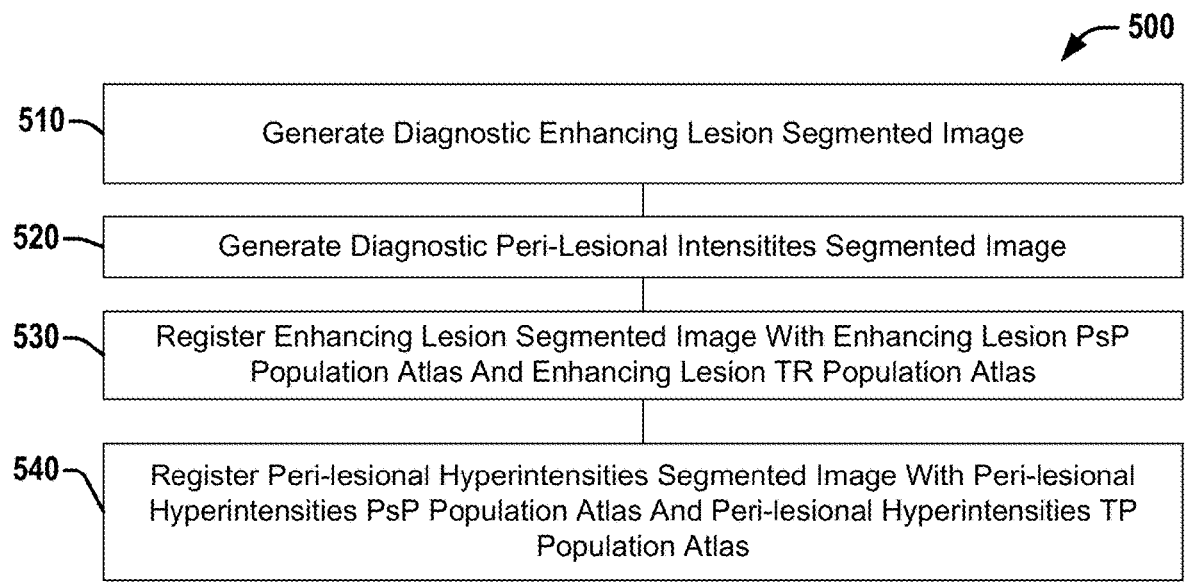
FIG. 5 illustrates a diagram of an example flow of a method or set of operations that registers a diagnostic mpMRI study with a population atlas according to various embodiments discussed herein.

Operations 400 also includes, at 420, generating a registered diagnostic multi-parametric MRI study based on the diagnostic multi-parametric MRI study. FIG. 5 illustrates a diagram of an example flow of a method or set of operations 500 that facilitates registering a diagnostic multi-parametric MRI study with a population atlas according to various embodiments discussed herein. In one embodiment, operations 500 includes, at 510, generating a diagnostic enhancing lesion segmented image by segmenting an enhancing lesion compartment represented in the diagnostic multi-parametric MRI study associated with the patient.

Operations 500 also includes, at 520, generating a diagnostic peri-lesional hyperintensities segmented image by segmenting a peri-lesional hyperintensities compartment represented in the diagnostic multi-parametric MRI study associated with the patient. In one embodiment, automated segmentation techniques, including for example, Deep-Medic brain tumor segmentation, CapTk segmentation, or a RADCNN technique may be employed to segment the peri-lesional hyperintensities compartment or the enhancing lesion compartment.

Operations 500 also includes, at 530, registering the diagnostic enhancing lesion segmented image with the enhancing lesion PsP population atlas and the enhancing lesion TP population atlas. In one embodiment, various registration techniques described herein, including, for example, mutual information with twelve degrees of information registration, may be employed. In another embodiment, other registration techniques may be employed.

Operations 500 further includes, at 540, registering the diagnostic peri-lesional hyperintensities segmented image with the peri-lesional hyperintensities PsP population atlas, and the peri-lesional hyperintensities TP population atlas. In one embodiment, various registration techniques described herein, including, for example, mutual information with twelve degrees of information registration, may be employed. In another embodiment, other registration techniques may be employed.

Returning to FIG. 4, operations 400 also includes, at 430, computing a probability that the patient will experience TP or PsP. The probability may be computed based on a comparison of the registered diagnostic mpMRI study with the enhancing lesion PsP population atlas, the peri-lesional hyperintensities PsP population atlas, the enhancing lesion TP population atlas, or the peri-lesional hyperintensities TP population atlas. In various embodiments, the probability can comprise one or more of a most likely outcome (e.g., as determined based on the comparison of the diagnostic mpMRI study with the atlases) such as whether a patient is likely to experience PsP or TP, a probability or confidence associated with a most likely outcome, and/or associated probabilities/confidences associated with each of a plurality of outcomes (e.g., PsP, TP).

In one embodiment, computing the probability includes computing a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas. In this embodiment, the DICE score may represent, in part, a score of overlap between the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas. In this example, a DICE score value of zero (0) indicates no spatial overlap with the segmented lesion and the atlases, while a DICE score value of one (1) indicates complete overlap. Higher overlap values with the PsP atlas indicate a higher likelihood that the patient associated with the diagnostic mpMRI study will experience PsP, while a higher overlap value with the TP atlas indicates a higher likelihood that the patient will experience TP. In one embodiment, the comparison is based on a mapping of the registered diagnostic enhancing lesion segmented image and the registered diagnostic peri-lesional hyperintensities segmented image into the atlas space (the enhancing lesion PsP population atlas space, the peri-lesional hyperintensities PsP population atlas, the enhancing lesion TP population atlas, and the peri-lesional hyperintensities TP population atlas) using an affine registration technique. In at least this way, embodiments provide a complementary image-based marker for identifying likelihood of occurrence of TP or PsP in GBM.

Operations 400 also includes, at 440, displaying the probability. Displaying the probability may include displaying the probability on a computer monitor, a smartphone display, a tablet display, or other displays. Displaying the probability may also include printing the probability.

In one embodiment, operations 400 also includes, at 450, generating a personalized GBM treatment plan based, at least in part, on the probability. In one embodiment, the personalized GBM treatment plan is further based on the diagnostic mpMRI study, or the DICE score. Generating a personalized GBM treatment plan facilitates delivering a particular treatment that will be therapeutically active to the patient, while minimizing negative or adverse effects experienced by the patient. For example, the personalized treatment plan may suggest a surgical treatment, may define a therapeutic agent dosage or schedule, when the patient is classified as likely to experience PsP. For a patient classified as likely to experience TP, other treatments may be suggested. In this embodiment, operations 400 further includes, at 460, optionally displaying the personalized GBM treatment plan.

Figure 6:
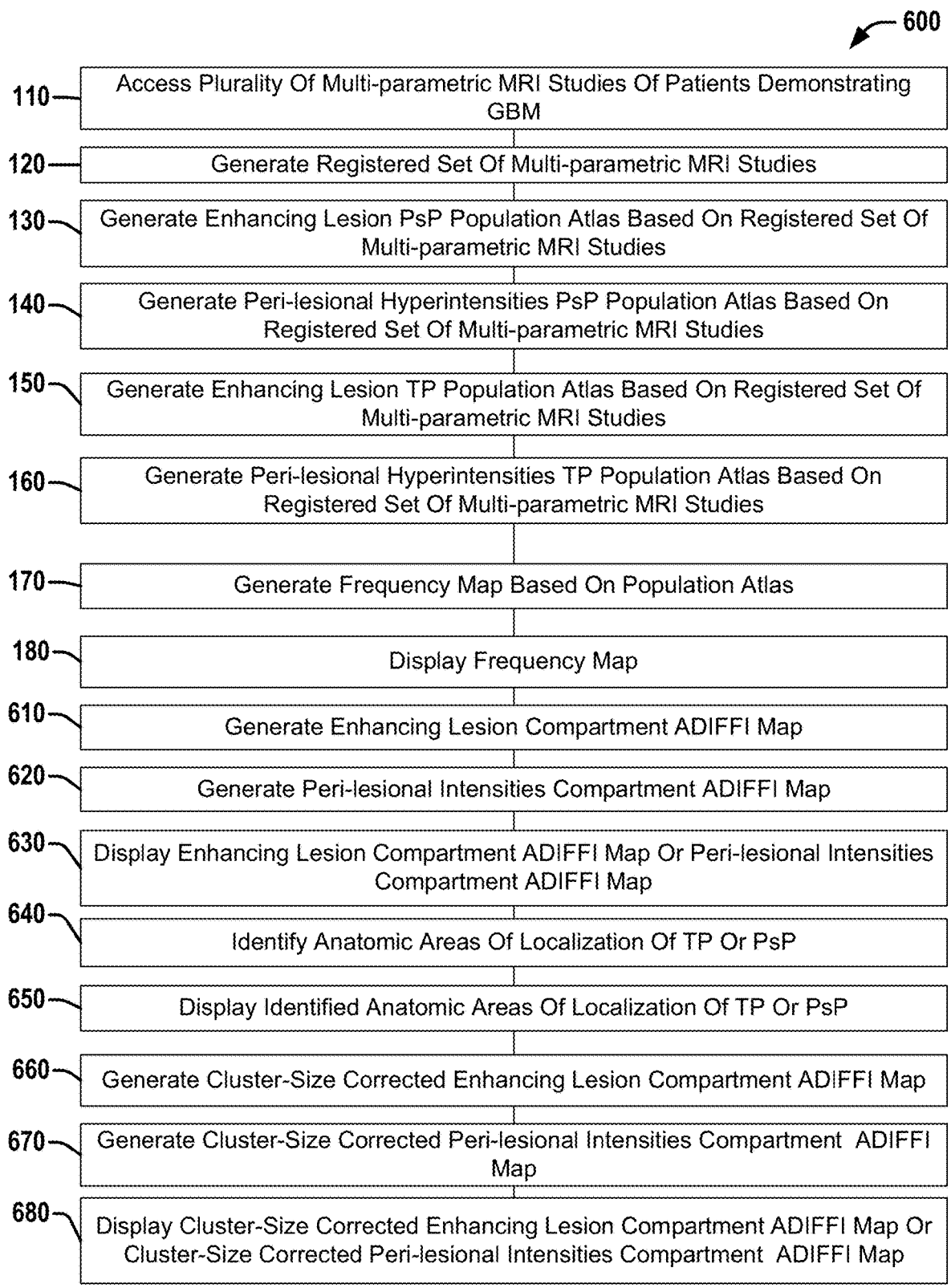
FIG. 6 illustrates a diagram of a third example flow of a method or set of operations that generates a quantitative population atlas of TP versus PsP, according to various embodiments discussed herein.

FIG. 6 illustrates a diagram of a third example flow of a method or set of operations 600 that generates a quantitative population atlas of TP versus PsP, according to various embodiments discussed herein. Operations 600 are similar to operations 100, but includes additional elements and details. Operations 600 includes operations 110-180. Operations 600 also includes, at 610, generating an enhancing lesion compartment analysis of differential involvement (ADIFFI) map based on the enhancing lesion PsP population atlas and the enhancing lesion TP population atlas.

Operations 600 also includes, at 620, generating a peri-lesional hyperintensities compartment ADIFFI map. The peri-lesional hyperintensities compartment ADIFFI map is based on the peri-lesional hyperintensities PsP population atlas and the peri-lesional hyperintensities TP population atlas.

Operations 600 further includes, at 630, displaying the enhancing lesion compartment ADIFFI map or the peri-lesional hyperintensities compartment ADIFFI map. Displaying the enhancing lesion compartment ADIFFI map or the peri-lesional hyperintensities compartment ADIFFI map may include displaying the enhancing lesion compartment ADIFFI map or the peri-lesional hyperintensities compartment ADIFFI map on a computer monitor, a smartphone display, a tablet display, or other displays. Displaying the enhancing lesion compartment ADIFFI map or the peri-lesional hyperintensities compartment ADIFFI map may also include printing the enhancing lesion compartment ADIFFI map or the peri-lesional hyperintensities compartment ADIFFI map.

In one embodiment, operations 600 may optionally include, at 640, identifying anatomic areas of localization of TP or PsP by partitioning the enhancing lesion compartment ADIFFI map or the peri-lesional hyperintensities compartment ADIFFI map using pre-labelled anatomical structures. Pre-labelled anatomical structures may be defined in the reference brain atlas space, for example, an MNI152 atlas. In this embodiment, operations 600 may further include, at 650, displaying the identified anatomic areas of localization of TP or PsP according to various embodiments described herein.

In one embodiment, operations 600 may optionally include, at 660, generating a cluster-size corrected enhancing lesion compartment ADIFFI map by performing a cluster-size correction of the enhancing lesion compartment ADIFFI map. In this embodiment, operations 600 also includes, at 670, generating a cluster-size corrected peri-lesional hyperintensities compartment ADIFFI map by performing a cluster-size correction of the peri-lesional hyperintensities compartment ADIFFI map. Embodiments may employ a random permutation (RP) analysis cluster size correction technique. Embodiments may employ RP-based cluster-size correction to identify distinct clusters occurring less than 5% by chance, thus facilitating the indication of distinct spatial differences between TP and PsP. In this embodiment, operations 600 further includes, at 680, displaying the cluster-size corrected enhancing lesion compartment ADIFFI map or the cluster-size corrected peri-lesional hyperintensities compartment ADIFFI map according to various embodiments described herein. Embodiments may designate statistically significant clusters as either PsP or TP by comparison of the cluster-size corrected ADIFFI maps with the peri-lesional hyperintensities PsP population atlas, the peri-lesional hyperintensities TP population atlas, the enhancing lesion PsP population atlas, or the enhancing lesion TP population atlas.

Techniques and aspects of various embodiments are further explained below, in connection with an example embodiment that facilitates generation of a quantitative population atlas of TP versus PsP in GBM, or the determination of a probability of a patient experiencing PsP or TP in GBM.

Example Use Case: Probabilistic Atlases of Post-treatment MPMRI Scans Reveal Distinct Hemispheric Distribution of GBM Progression Versus Pseudo-Progression In one example, 105 post-treatment multi-parametric MRI studies (34 PsP, 71 TP) were collected from two institutions. Confirmation for PsP and TP was obtained either from pathologic resection or MRI follow-up using RANO criteria. Scans were registered to a T1-weighted brain atlas (MNI152), followed by expert delineation of enhancing lesion on Gd-T1w MRI and peri-lesional hyperintensities on T2/FLAIR. hi another embodiment, delineation (segmentation) of enhancing lesions may be performed automatically. Population atlases quantifying the frequency of occurrence of enhancing lesion and peri-lesional hyperintensities were constructed by averaging voxel intensities across the patients. Analysis of differential involvement (ADIFFI) based on a two-tailed Fisher's exact test was performed to compute significant differences (p-value<0.05) across PsP and TP voxels. Significant clusters were finally mapped to a structural atlas to provide anatomic localization of TP and PsP lesions.

In this embodiment, ADIFFI results showed TP prominence in the right parietal lobe with 75% occurrence in enhancing lesion and 61% in peri-lesional T2/FLAIR hyperintensities. PsP lesions were prominent in the left hemisphere, with peri-lesional T2/FLAIR hyperintensities having a multi-focal spatial distribution in the temporal lobe, insula, and putamen, and enhancing lesion being localized at the temporal lobe.

Embodiments anatomically localize GBM by employing "population atlases" of GBM phenotypes (PsP, TP) on MRI (including post-treatment or pre-treatment MRI) to establish predisposition of tumor progression or PsP to specific spatial locations in the brain based on their frequency of occurrence. The statistical population atlases generated according to various embodiments described herein allow for the succinct encapsulation of structural and anatomical variability of the disease across a patient population using a single reference or canonical representation. No existing approaches have attempted to employ population atlases of lesion locations to capture the likelihood of occurrence of tumor progression and PsP on routine post-treatment or pre-treatment mpMRI scans as described herein.

In one embodiment, population atlases on a cohort of 105 brain multi-parametric MRI (mpMRI) scans across two lesion sub-compartments: peritumoral hyperintensities as defined on FLAIR and $T_{2w}$ MRI scans, and enhancing lesion as defined on $T_{1w}$ MRI, are constructed to quantify the frequency of occurrence of PsP and tumor progression in post-treatment lesions. These lesion sub-compartments capture the tumor or lesion biology by depicting differences in intensity profiles across multi-parametric MRI scans and provide cues regarding associations between specific locations and the specific disease phenotype. Embodiments further employ a statistical mapping technique, ADIFFI, to identify the statistically significant lesion locations across the two post-treatment disease pathologies.

Figure 7:
FIG. 7 illustrates a summary of a study population use to generate a quantitative population atlas of tumor progression TP versus PsP, according to various aspects discussed herein.

In one embodiment, an Institutional Review Board-approved and HIPAA-compliant study population comprised a GBM patient population from two different institutions, Cleveland Clinic and Dana-Farber/Brigham and Women's Cancer Center (DF/BWCC). The studies were identified by performing a retrospective review of all brain tumor patients who received chemo-radiation treatment using the Stupp protocol at the respective institutions, and who had an enhancing lesion within three months of treatment. Patients who were prescribed bevacizumab were excluded from the study. The population cohort included 71 tumor progression cases (38 from Cleveland Clinic and 33 from DF/BWCC), as well as 34 PsP cases (21 from Cleveland Clinic and 13 from DF/BWCC). All cases were confirmed for disease presence using the criteria provided below. Informed consent was obtained for all patients involved in the study. All MR scans were acquired using either a 1.5 Tesla or a 3-Tesla scanner. Referring to FIG. 7, table 710 summarizes the demographics for this study population.

In one example embodiment, inclusion criteria consisted of the following: (1) availability of all 3 routine MRI sequences (Gd-$T_{1w}$, $T_{2w}$, FLAIR), (2) MRI scans with diagnostic image quality as determined by collaborating radiologists, and (3) patients with a post-treatment enhancing lesion with more than 5 millimeters (mm) of rim or nodular enhancement, and availability of diagnostic reads of the lesion as belonging to PsP or tumor progression following disease confirmation. Confirmation for tumor progression or pseudo-progression was obtained either by histological analysis in some cases or by follow-up imaging. Continued increase in enhancing tumor size within the subsequent 6-month period was considered progression (TP), while reduction in tumor size within the subsequent 6-month period was considered pseudo-progression.

Embodiments register images and segment tumors or lesions represented in the images. In one embodiment, annotations were conducted for lesions on the MRI volume. Lesions were annotated into two regions: enhancing lesion compartment and $T_{2w}$/FLAIR hyperintense peri-lesional compartment. Gd-$T_{1w}$ MRI scans were used to delineate the enhancing lesion compartment, while both $T_{2w}$ and FLAIR scans were used to annotate the $T_{2w}$/FLAIR hyperintense peri-lesional compartment. In one embodiment, annotations were performed by two experienced readers via an open source hand-annotation tool in 3D Slicer. In another embodiment, annotation may be performed automatically using, for example, machine learning techniques. Example segmentation or annotation techniques that may be employed include, for example, DeepMedic brain tumor segmentation, CapTk segmentation, or a RADCNN technique.

In order to map scans to the same space for the purpose of spatial atlas construction, the three MRI sequences for a patient, Gd-$T_{1w}$ MRI, $T_{2w}$, and FLAIR, were co-registered to a 1.0-mm isotropic T1-weighted brain atlas (MNI152; Montreal Neurological Institute) using mutual information with 12-degrees of freedom. This was followed by visual inspection to make sure images were properly aligned. Skull stripping was then performed using a deformable surface classification algorithm, followed by bias field correction that was performed using a nonparametric non-uniform intensity normalization technique.

Embodiments construct a frequency map. In one embodiment, from the available annotations for both enhancing lesion and $T_{2w}$/FLAIR hyperintense peri-lesional compartments, separate population atlases for each compartment were built for both pathologies (tumor progression and PsP). These atlases quantify the frequency of occurrence of both enhancing lesion and peri-lesional hyperintensities across tumor progression and PsP, by averaging intensity values for voxels across the annotated binary images of patients involved in the study. In one embodiment, the frequency of lesion occurrence was visualized using a heat map superimposed on the reference MNI152 atlas.

From the constructed tumor progression (TP) frequency atlases and PsP frequency atlases, analysis of differential involvement (ADIFFI) was performed, once for the enhancing lesion compartment and once for the peri-lesional hyperintensities compartment. ADIFFI of the tumor progression frequency atlases and PsP frequency atlases demonstrates that there are areas in the brain that are statistically significantly more likely to experience PsP or to experience TP. In this example, first, a two-tailed Fisher's exact test was conducted, to evaluate a 2×2 contingency table that compares tumor progression/PsP along with tumor/non-tumor occurrence for each voxel across all patients, illustrated in FIG. 8 at table 810. From this voxel-wise analysis, significance level was then measured, and the voxels that yielded p-value<0.05 were stored. The voxel-wise probabilities according to Fisher's exact test are computed using the following formula:

$$p = \frac{(a+b)!(c+d)!(a+c)!(b+d)!}{a!b!c!n!}.$$

In this example, a represents the number of tumor progression as well as the lesion positive occurrences across all subjects at the current voxel, b represents the number of tumor progression as well as the lesion-negative occurrences across all subjects at the current voxel, crepresents the number of PsP as well as the lesion positive across all subjects at the current voxel, d represents the number of PsP as well as the lesion-negative occurrences across all subjects at the current voxel, and n represents the total number of studies.

Next, connected component analysis was applied to cluster significant voxels found across the two compartments (enhancing lesion compartment, peri-lesional hyperintensities compartment) for both tumor progression and PsP that appeared on the ADIFFI maps, for enhancing lesion as well as for peri-lesional hyperintensities. The brain was finally partitioned using pre-labeled anatomical structures in MNI space, for the purpose of identifying the anatomic areas of localization for tumor progression/PsP across subjects.

Figure 8:
FIG. 8 illustrates a 2×2 contingency table that compares lesion progression/PsP along with lesion/non-lesion occurrence for each voxel across a population of patients, according to various embodiments discussed herein.

Table 810 in FIG. 8 illustrates a 2×2 contingency table constructed for a two-tailed Fisher's exact test for each voxel of the tumor progression and PsP atlases. In table 810, (a) represents the number of tumor progression as well as the lesion positive occurrences across subjects at the current voxel, (b) represents the number of tumor progression as well as the lesion-negative occurrences across subjects at the current voxel, (c) represents the number of PsP as well as the lesion positive across subjects at the current voxel, and (d) represents the number of PsP as well as the lesion-negative occurrences across subjects at the current voxel.

Embodiments may perform comparison corrections to account for the extensive number of voxel-wise calculations performed during ADIFFI. In this example, embodiments perform cluster-size correction using random permutation analysis. In one embodiment, after ADIFFI was performed, random permutation (RP) analysis was conducted for cluster size correction in order to obtain the final ADIFFI map. Specifically, $T_{2w}$/FLAIR hyperintense peri-lesional components across the two categories (tumor progression/PsP) were randomly reassigned to one of these pathologies, then ADIFFI was re-conducted, and voxels with p-values less than 0.05 were stored. In addition, the sizes of statistically significant clusters were documented. In this example, the process was iterated 500 times, while in another example, other, different numbers of iterations may be employed. Random permutation analysis was employed in order to identify distinct clusters occurring less than 5% by chance, which provide distinct spatial differences between tumor progression and PsP. This analysis was conducted only on $T_{2w}$/FLAIR hyperintense peri-lesional components, since these are significantly larger than enhancing lesion components; therefore, resulting clusters would better help draw statistical measures.

Finally, statistically significant clusters appearing on the final ADIFFI maps were designated as either PsP or true progression by referring to the population atlases that were individually constructed for tumor progression and PsP. More specific anatomic localization was then obtained from the final ADIFFI maps that were also mapped to a structural atlas.

Figure 9:
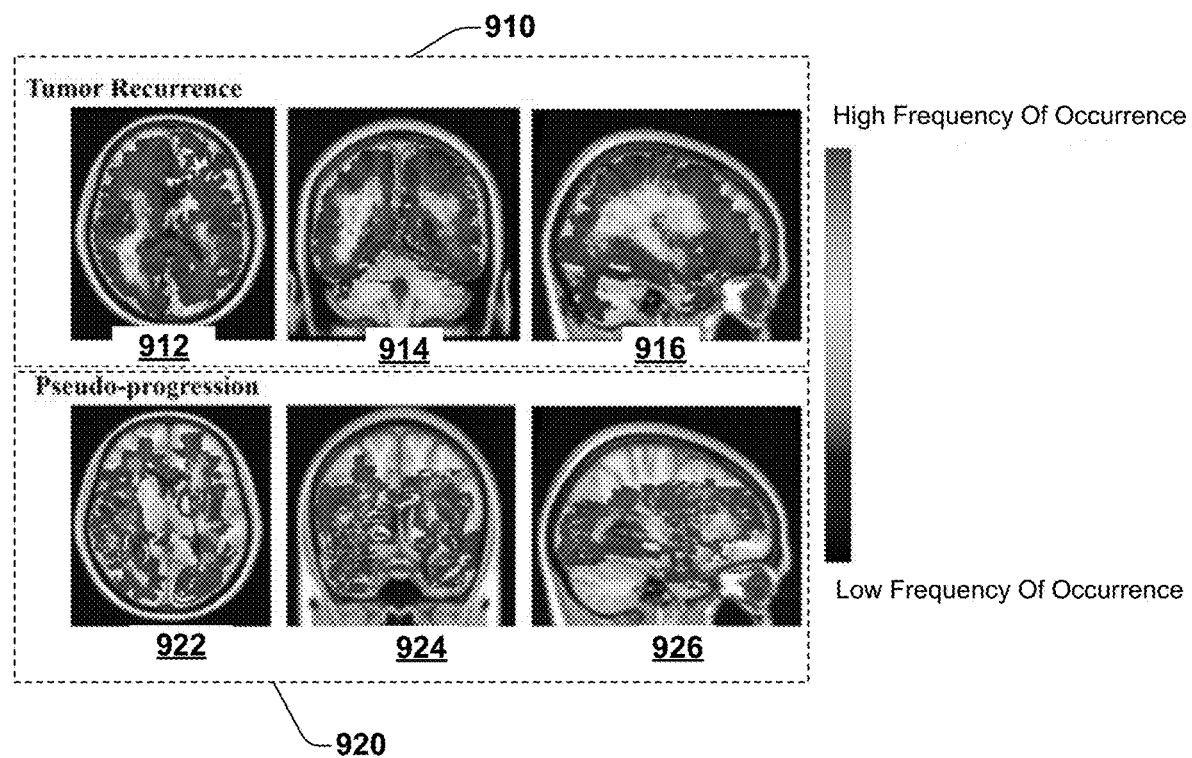
FIG. 9 illustrates frequency maps of tumor occurrence for peri-lesional T2/FLAIR hyperintensities in tumor progression, according to various embodiments discussed herein.
Figure 10:
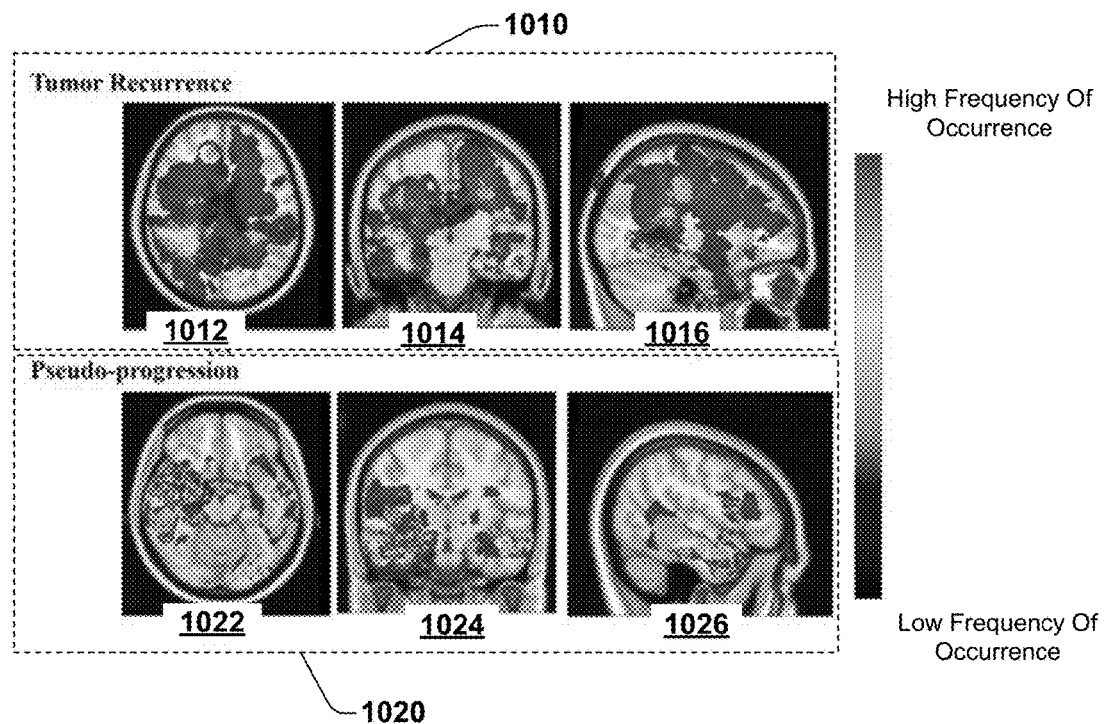
FIG. 10 illustrates frequency maps of tumor occurrence for enhancing lesion areas in tumor progression according to various embodiments discussed herein.

The resulting frequency maps that were constructed for both $T_{2w}$/FLAIR hyperintense peri-lesional and enhancing lesion areas are shown in FIG. 9 and FIG. 10 respectively. FIG. 9 and FIG. 10 show that tumor progression in both compartments (enhancing lesion and $T_{2w}$/FLAIR hyperintense peri-lesional) is more likely in the right hemisphere, whereas PsP is more likely in the left hemisphere.

The frequency maps obtained for peri-lesional T2/FLAIR hyperintensities from the associated generated atlases show that true progression is more likely in the right hemisphere, with a frequency of occurrence of 61% at the parietal lobe and 22% at the frontal lobe, illustrated in FIGS. 9 at 912, 914, and 916. Frequency maps obtained for the enhancing lesion compartment also reveal that true progression is more likely in the right hemisphere, with 75% frequency of occurrence in the parietal lobe and 25% in the temporal lobe, illustrated in FIGS. 10 at 1012, 1014, and 1016. These results suggest that tumor progression exhibits right hemispheric lobar prominence across the population atlases.

PsP, unlike true progression, is more likely in the left hemisphere in the analysis of peri-lesional T2/FLAIR hyperintensities, with frequencies of occurrence of 37% in the temporal lobe, 19% in the insula, and 15% in the putamen, illustrated in FIGS. 9 at 922, 924, and 926. In the analysis of the enhancing lesion regions, PsP appears to be more likely within the left hemisphere, with 85% frequency of occurrence in the temporal lobe, illustrated in FIGS. 10 at 1022, 1024, and 1026.

FIG. 9 illustrates frequency maps of tumor occurrence for peri-lesional T2/FLAIR hyperintensities in tumor progression 910 with, at 912 axial, 914 coronal, and 916 sagittal views, where lobar prominence is shown in the right parietal lobe. Pseudo progression is illustrated at 920, with 922 axial, 924 coronal, and 926 sagittal views, where a multi-focal spatial distribution is present.

FIG. 10 illustrates frequency maps of tumor occurrence for enhancing lesion areas in tumor progression 1010 with 1012 axial, 1014 coronal, and 1016 sagittal views, where lobar prominence is shown in the right parietal lobe. Pseudo-progression is illustrated at 1020, with 1022 axial, 1024 coronal, and 1026 sagittal views, where lobar prominence is shown in the left temporal lobe.

Figure 11:
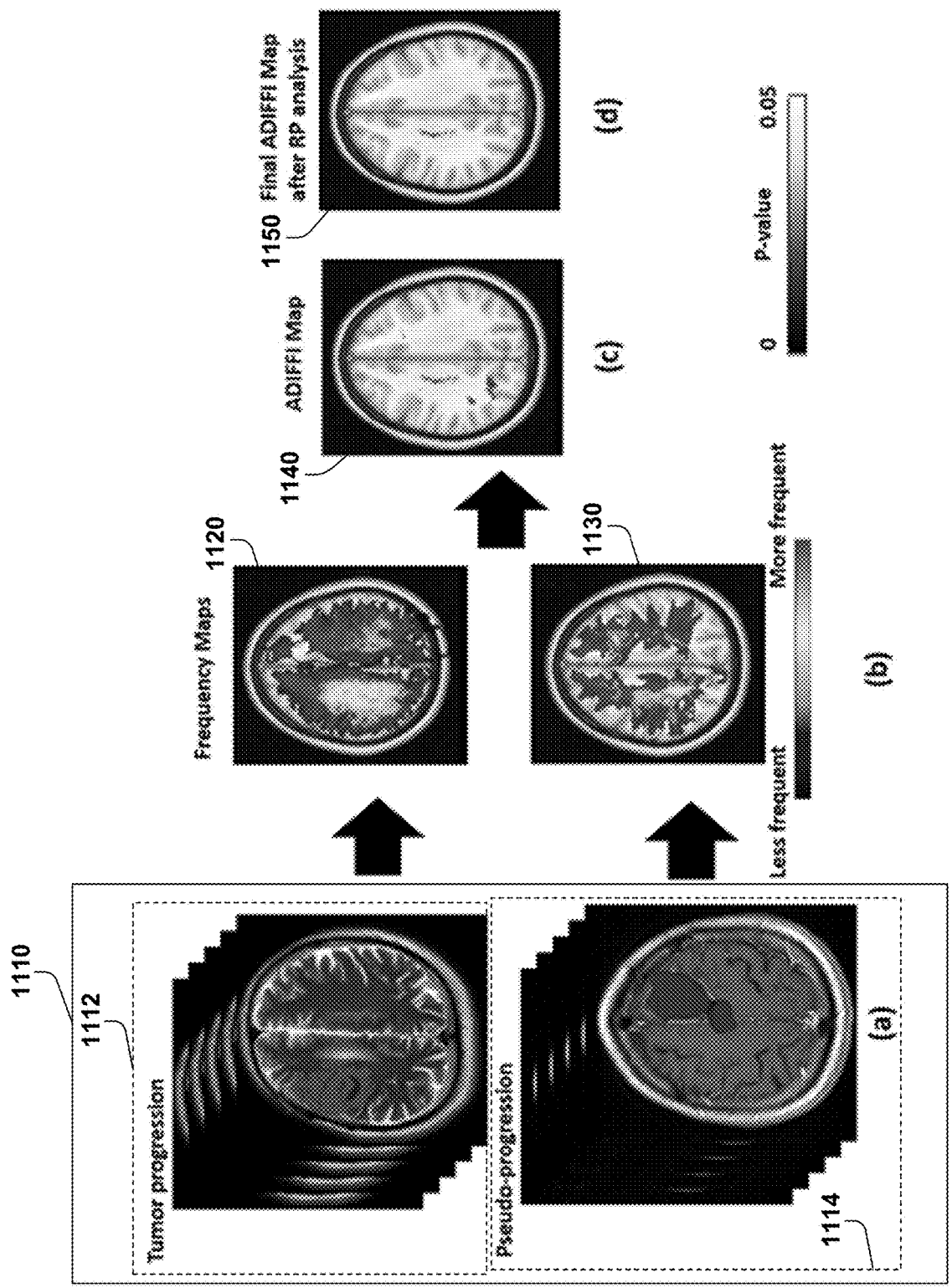
FIG. 11 illustrates a workflow according to various embodiments discussed herein.

FIG. 11 illustrates a workflow for embodiments described herein. FIG. 11 illustrates at 1110 a plurality of multi-parametric MRI studies of patients demonstrating GBM. FIG. 11 illustrates, at 1112 MRI T2-weighted volumes for tumor progression and at 1114 contrast-enhanced T1-weighted volumes for pseudo-progression. Frequency maps of tumor occurrence for peri-lesional T2/FLAIR hyperintensities tumor progression are illustrated at 1120 and for pseudo-progression at 1130. ADIFFI map 1140 is obtained using Fisher's exact test level of significance as described herein. Final ADIFFI map(s) 1150 are obtained after cluster size correction using random permutation analysis as described herein.

Random permutation (RP) analysis conducted on the 105 cases in this example revealed that the average and standard deviation of maximum cluster size are 3310 and 1723.9 voxels respectively. Also, 95% of the cluster sizes were smaller than 6258 voxels, meaning that clusters larger than this size threshold would occur in less than 5% of all random permutations. This resulted in a distinct $T_{2w}$/FLAIR hyperintense peri-lesional cluster size of 6700 voxels, localized at the right parietal lobe and associated with tumor progression. The designation of PsP or true progression based on ADIFFI maps as for each significant voxel/cluster was accomplished by referring to the population atlases of both compartments (enhancing lesion, $T_{2w}$/FLAIR hyperintense peri-lesion) that were individually constructed for tumor progression and PsP. The final ADIFFI map obtained after RP analysis as well as the entire pipeline is shown in FIG. 11.

Distinguishing tumor progression (TP) from pseudo-progression (PsP) is a substantial problem in GBM management. As demonstrated by the examples and embodiments described herein, various embodiments can facilitate improved discrimination of patients who are likely to experience TP from patients who are likely to experience PsP based on probabilistic atlases constructed from mpMRI studies of patient brains, as shown in MRI images. The ability to identify patients likely to experience TP or likely to experience PsP can provide a pre-treatment indicator of response and anatomic features that can be targeted by various therapeutic techniques. Embodiments may facilitate determining, for a patient demonstrating GBM, that tumor progression, being an aggressive condition, may have hemispheric, and lobe-specific proclivity, which will likely be distinct from that for patients with a benign PsP lesion, on mpMRI scans, including post-treatment mpMRI scans or pre-treatment mpMRI scans. Embodiments may facilitate determining, for a patient, that likelihood of tumor progression is more consistent with lesions occurring in the right hemisphere, based on the analysis of both enhancing lesion and peri-lesional T2/FLAIR hyperintensities, on post-treatment mpMRI scans or pre-treatment mpMRI scans. Embodiments may facilitate determining, for a patient, that tumor progressions have a parietal lobe prominence when analyzing enhancing lesion and peri-lesional T2/FLAIR hyperintensities, on post-treatment MRI scans or pre-treatment MRI scans. PsP, on the other hand, appears to be more likely in the left hemisphere. Further, no lobar-specific distribution in PsP was observed when analyzing T2/FLAIR hyperintensities in post-treatment scans. Embodiments may further provide clinical decision support in management of GBM by computing a probability that a patient will experience TP or PsP based, at least in part, on a comparison of a diagnostic mpMRI study of the patient brain with atlases generated according to various embodiments described herein.

In various example embodiments, method(s) discussed herein can be implemented as computer executable instructions. Thus, in various embodiments, a computer-readable storage device can store computer executable instructions that, when executed by a machine, for example a computer or processor, cause the machine to perform methods or operations described or claimed herein including operation(s) described in connection with methods or operations 100, 200, 300, 400, 500, 600, or 1400, or any other methods or operations described herein. While executable instructions associated with the listed methods or operations are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to generating a quantitative population atlas of TP versus PsP or determining a probability that a patient will experience PsP or TP are based on features are not perceivable by the human eye, and their computation cannot be practically performed in the human mind. A probabilistic atlas of multi-parametric MRI scans as described herein cannot be implemented in the human mind or with pencil and paper, for at least the reason that a human mind cannot store a multi-parametric MRI study of a human brain. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance, including at least the predictive accuracy, of the machine, computer, or system with which embodiments are implemented.

Figure 12:
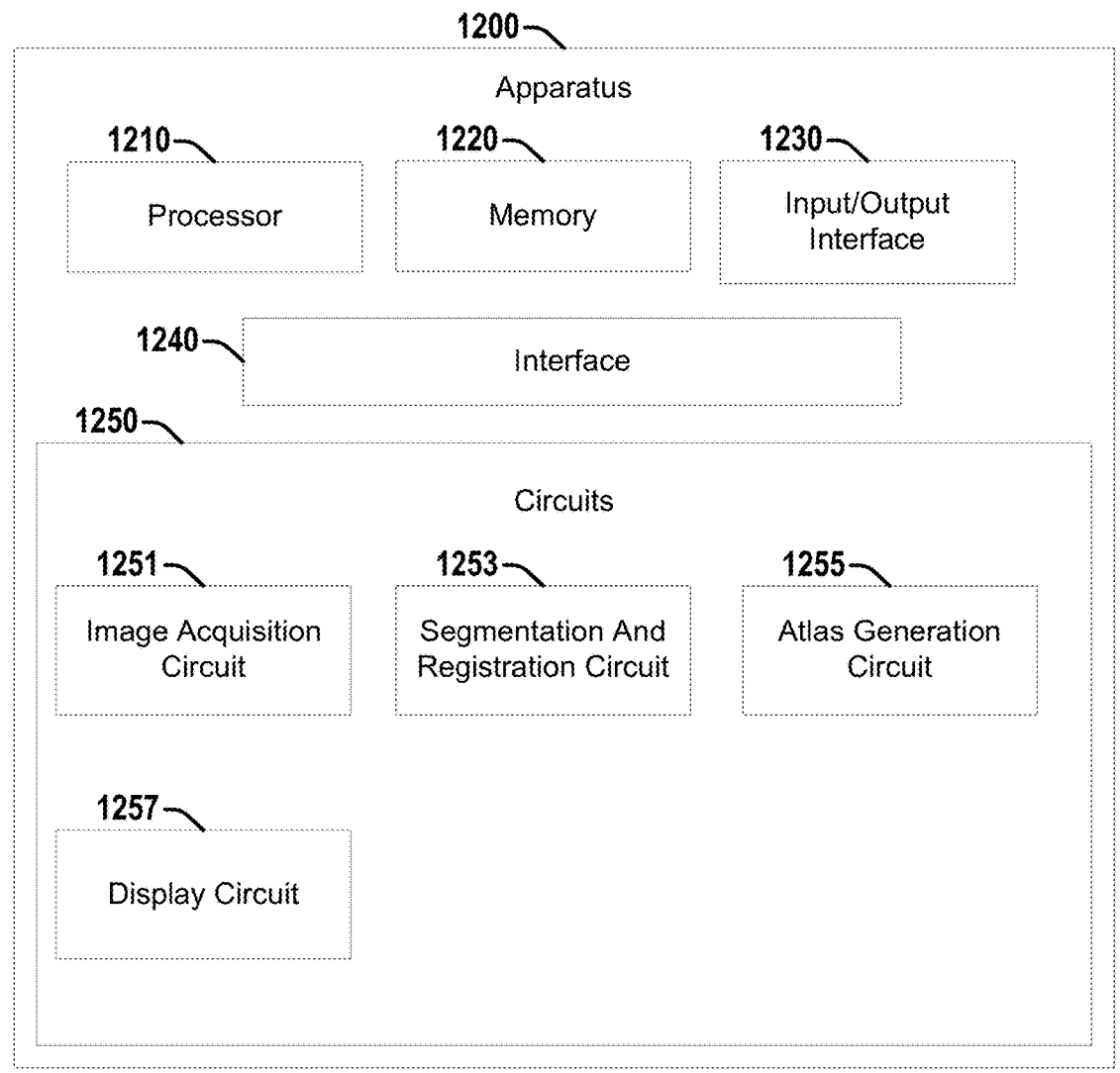
FIG. 12 illustrates a diagram of a first example apparatus that can facilitate generating a quantitative population atlas of TP versus PsP, according to various embodiments discussed herein.

Referring to FIG. 12, illustrated is a diagram of a first example apparatus 1200 that can facilitate generating a quantitative population atlas of TP versus PsP, according to various embodiments discussed herein. Apparatus 1200 can be configured to perform various techniques discussed herein, for example, generating a quantitative population atlas of TP versus PsP based on a plurality of mpMRI studies of patients demonstrating GBM, or to compute a probability that a patient will experience TP or PsP based on a diagnostic mpMRI study associated with the patient, and/or employing such a quantitative population atlas of TP versus PsP to generate a probability of TP or PsP based on comparison with the diagnostic mpMRI study. Apparatus 1200 includes a processor 1210. Apparatus 1200 also includes a memory 1220. Processor 1210 can, in various embodiments, include circuitry such as, but not limited to, one or more single-core or multi-core processors. Processor 1210 can include any combination of general-purpose processors and dedicated processors (e.g., graphics processors, application processors, etc.). The processor(s) can be coupled with and/or can comprise memory (e.g., memory 1220) or storage and can be configured to execute instructions stored in the memory 1220 or storage to enable various apparatus, applications, or operating systems to perform operations and/or methods discussed herein. Memory 1220 can be configured to store one or more radiological images (e.g., MRI, CT, PET, SPECT, etc.). Each of the radiological image(s) can have a plurality of voxels, each voxel having an associated intensity. In some embodiments, memory 1220 can store a plurality of multi-parametric MRI studies of a population of patients demonstrating GBM, or a quantitative population atlas of TP vs PsP, while in the same or other embodiments, memory 1220 can store a radiological image or diagnostic mpMRI study of a patient demonstrating GBM for whom a probability of PsP or TP is to be determined. Memory 1220 can be further configured to store metadata or one or more clinical features associated with the patient.

Apparatus 1200 also comprises an input/output (I/O) interface 1230, for example, associated with one or more I/O devices, a set of circuits 1250, and an interface 1240 that connects the processor 1210, the memory 1220, the I/O interface 1230, and the set of circuits 1250. I/O interface 1230 can be configured to transfer data between memory 1220, processor 1210, circuits 1250, and external devices, for example, a medical imaging device such as an MRI system or apparatus.

The set of circuits 1250 may include an image acquisition circuit 1251, a segmentation and registration circuit 1253, an atlas generation circuit 1255, and a display circuit 1257. Image acquisition circuit 1251 is configured to access one or more radiological images, for example, a plurality of mpMRI studies of a population of patients demonstrating GBM, or a diagnostic mpMRI study of a patient demonstrating GBM for whom a probability of PsP or TP is to be determined. Accessing the radiological image(s) can comprise accessing radiological image(s) stored in memory 1220. In one embodiment, accessing the radiological image(s) can include accessing radiological image(s) stored in a data storage device, including a hard disk drive, a solid-state device, a tape drive, or accessing radiological image(s) over a local area network. Accessing the radiological image(s) can comprise acquiring electronic data, reading from a computer file, receiving a computer file, reading from a computer memory, or other computerized activity not practically performed in the human mind.

Segmentation and registration circuit 1253 is configured to generate a registered set of mpMRI studies. In one embodiment, segmentation and registration circuit 1253 is configured to generate the registered set of mpMRI studies by, for each member of the plurality of mpMRI studies, respectively: generating an enhancing lesion segmented image by segmenting an enhancing lesion compartment represented in a first MRI image acquired during a first MRI sequence of a member of the plurality of multi-parametric MRI studies associated with a patient; generating a peri-lesional hyperintensities segmented image by segmenting a peri-lesional hyperintensities compartment represented in a second, different MRI image acquired during a second, different MRI sequence of the member of the plurality of multi-parametric MRI studies associated with the patient. Segmentation and registration circuit 1253 is further configured to generate the registered set of mpMRI studies by, for each member of the plurality of mpMRI studies, respectively: registering the enhancing lesion segmented image and the peri-lesional hyperintensities segmented image with a reference brain atlas. The reference brain atlas may be, in one embodiment, an MNI152 brain atlas. In another embodiment, another, different reference brain atlas may be employed.

Atlas generation circuit 1255 is configured to generate an enhancing lesion PsP population atlas by computing a voxel-wise frequency of occurrence of enhancing lesion of the members of the registered set of mpMRI studies associated with patients who demonstrated PsP. In one embodiment, atlas generation circuit 1255 is configured to compute the voxel-wise frequency of occurrence of enhancing lesion of the members of the registered set of mpMRI studies associated with patients who demonstrated PsP by computing the average intensity value for each voxel of each annotated or segmented enhancing lesion image of each mpMRI study associated with patients who demonstrated PsP.

Atlas generation circuit 1255 is further configured to generate a peri-lesional hyperintensities PsP population atlas by computing a voxel-wise frequency of occurrence of peri-lesional hyperintensities of the members of the registered set of mpMRI studies associated with patients who demonstrated PsP. In one embodiment, atlas generation circuit 1255 is configured to compute the voxel-wise frequency of occurrence of peri-lesional hyperintensities of the members of the registered set of mpMRI studies associated with patients who demonstrated PsP by computing the average intensity value for each voxel of each annotated or segmented peri-lesional hyperintensities image of each multiparametric study associated with patients who demonstrated PsP.

Atlas generation circuit 1255 is further configured to generate an enhancing lesion TP population atlas by computing a voxel-wise frequency of occurrence of enhancing lesion of the members of the registered set of mpMRI studies associated with patients who demonstrated TP. In one embodiment, atlas generation circuit 1255 is configured to compute the voxel-wise frequency of occurrence of enhancing lesion of the members of the registered set of mpMRI studies associated with patients who demonstrated TP based on the registered set of mpMRI studies by computing the average intensity value for each voxel of each annotated or segmented enhancing lesion image of each multiparametric study associated with patients who demonstrated TP.

Atlas generation circuit 1255 is further configured to generate a peri-lesional hyperintensities TP population atlas by computing a voxel-wise frequency of occurrence of peri-lesional hyperintensities of members of the registered set of mpMRI studies who demonstrated TP. In one embodiment, atlas generation circuit 1255 is configured to compute the voxel-wise frequency of occurrence of peri-lesional hyperintensities of the members of the registered set of mpMRI studies associated with patients who demonstrated TP based on the registered set of mpMRI studies by computing the average intensity value for each voxel of each annotated or segmented peri-lesional hyperintensities image of each mpMRI study associated with patients who demonstrated TP.

Display circuit 1257 is configured to generate a frequency map for at least one of the enhancing lesion PsP population atlas, the peri-lesional hyperintensities PsP population atlas, the enhancing lesion TP population atlas, or the peri-lesional hyperintensities TP population atlas. Display circuit 1257 is further configured to display the frequency map. In one embodiment, displaying the frequency map includes displaying the frequency map superimposed with the reference brain atlas.

Figure 13:
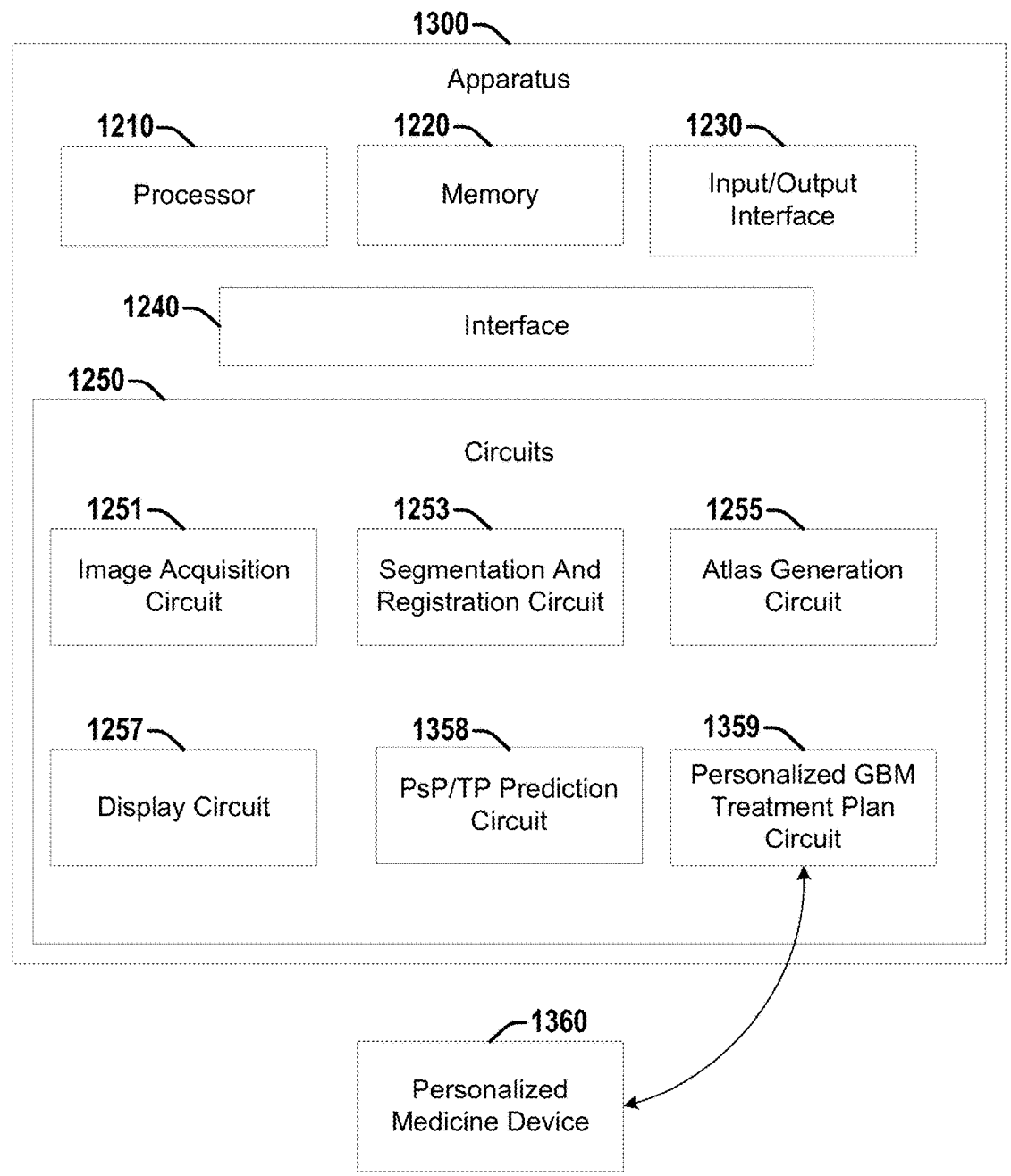
FIG. 13 illustrates a diagram of a second example apparatus that can facilitate generating a quantitative population atlas of TP versus PsP, according to various embodiments discussed herein.

Referring to FIG. 13 illustrated is a diagram of a second example apparatus 1300 that can facilitate generating a quantitative population atlas of TP versus PsP based on a plurality of mpMRI studies of patients demonstrating GBM, or to compute a probability that a patient will experience TP or PsP based on a diagnostic mpMRI study associated with the patient, according to various embodiments discussed herein. Example apparatus 1300 is similar to the example apparatus 1200 of FIG. 12, including elements 1210-1257, but comprises additional details and elements. Apparatus 1300 includes PsP/TP Prediction circuit 1358, and personalized GBM treatment plan circuit 1359.

PsP/TP Prediction circuit 1358 is configured to access a diagnostic multi-parametric MRI (mpMRI) study associated with a patient demonstrating GBM. The diagnostic mpMRI study includes a plurality of MRI images, where a member of the plurality of MRI images includes a plurality of associated voxels, a voxel having an intensity. A first member of the plurality of MRI images may be acquired according to a first MRI sequence, for example, one of $Gd$-$T_{1w}$. A second, different member of the plurality of MRI images may be acquired according to a second, different MRI sequence, for example, $T_{2w}$, or FLAIR.

PsP/TP Prediction circuit 1358 is also configured to generate a registered diagnostic mpMRI study based on the diagnostic multi-parametric MRI study. PsP/TP Prediction circuit 1358 is configured to generate a registered diagnostic mpMRI study by: generating a diagnostic enhancing lesion segmented image by segmenting an enhancing lesion compartment represented in the diagnostic mpMRI study associated with the patient; generating a diagnostic peri-lesional hyperintensities segmented image by segmenting a peri-lesional hyperintensities compartment represented in the diagnostic mpMRI study associated with the patient. PsP/TP Prediction circuit 1358 may be further configured to register the diagnostic enhancing lesion segmented image with the enhancing lesion PsP population atlas and the enhancing lesion TP population atlas; and register the diagnostic peri-lesional hyperintensities segmented image with the peri-lesional hyperintensities PsP population atlas, and the peri-lesional hyperintensities TP population atlas.

PsP/TP Prediction circuit 1358 is also configured to compute a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas. PsP/TP Prediction circuit 1358 is further configured compute a probability that the patient will experience TP or PsP based on the DICE score. In this embodiment, display circuit 1257 is further configured to optionally display the probability or the DICE score. In one embodiment, PsP/TP Prediction circuit 1358 may be configured to compute the probability using machine learning techniques. For example, PsP/TP Prediction circuit 1358 may be configured to compute the probability using a support vector machine (SVM) machine learning technique, a quadratic discriminant analysis (QDA) machine learning technique, a linear discriminant analysis (LDA) machine learning technique, a random forests technique, or as a convolutional neural network (CNN).

Apparatus 1300 can also include personalized GBM treatment plan circuit 1359. Personalized GBM treatment plan circuit 1359 can be configured to generate a personalized GBM treatment plan based, at least in part, on a probability obtained from PsP/TP prediction circuit 1358. Personalized GBM treatment plan circuit 1359 can be configured to generate a personalized GBM treatment plan for the patient of whom the diagnostic mpMRI study was acquired based, at least in part, on the probability derived therefrom. Defining a personalized GBM treatment plan facilitates delivering a particular treatment that will be therapeutically active to the patient, while minimizing negative or adverse effects experienced by the patient. For example, the personalized GBM treatment plan may suggest a first surgical treatment, may suggest a first pharmaceutical agent dosage or schedule, and/or other treatments for a patient determined to likely experience PsP, while the personalized GBM treatment plan may suggest a second, different surgical treatment, a second different pharmaceutical agent dosage or schedule, to a patient determined to likely experience TP.

Apparatus 1300 can further include personalized medicine device 1360. Apparatus 1300 can be configured to provide the probability, DICE score, diagnostic mpMRI study, personalized GBM treatment plan, or other data to personalized medicine device 1360. Personalized medicine device 1360 may be, for example, a computer assisted diagnosis (CADx) system or other type of personalized medicine device that can be used to facilitate the prediction of PsP or TP in GBM, or to facilitate the generation of a probabilistic GBM population atlas as described herein. In one embodiment, personalized GBM treatment plan circuit 1359 can control personalized medicine device 1360 to display the probability, personalized GBM treatment plan, or other data on a computer monitor, a smartphone display, a tablet display, or other displays.

Figure 14:
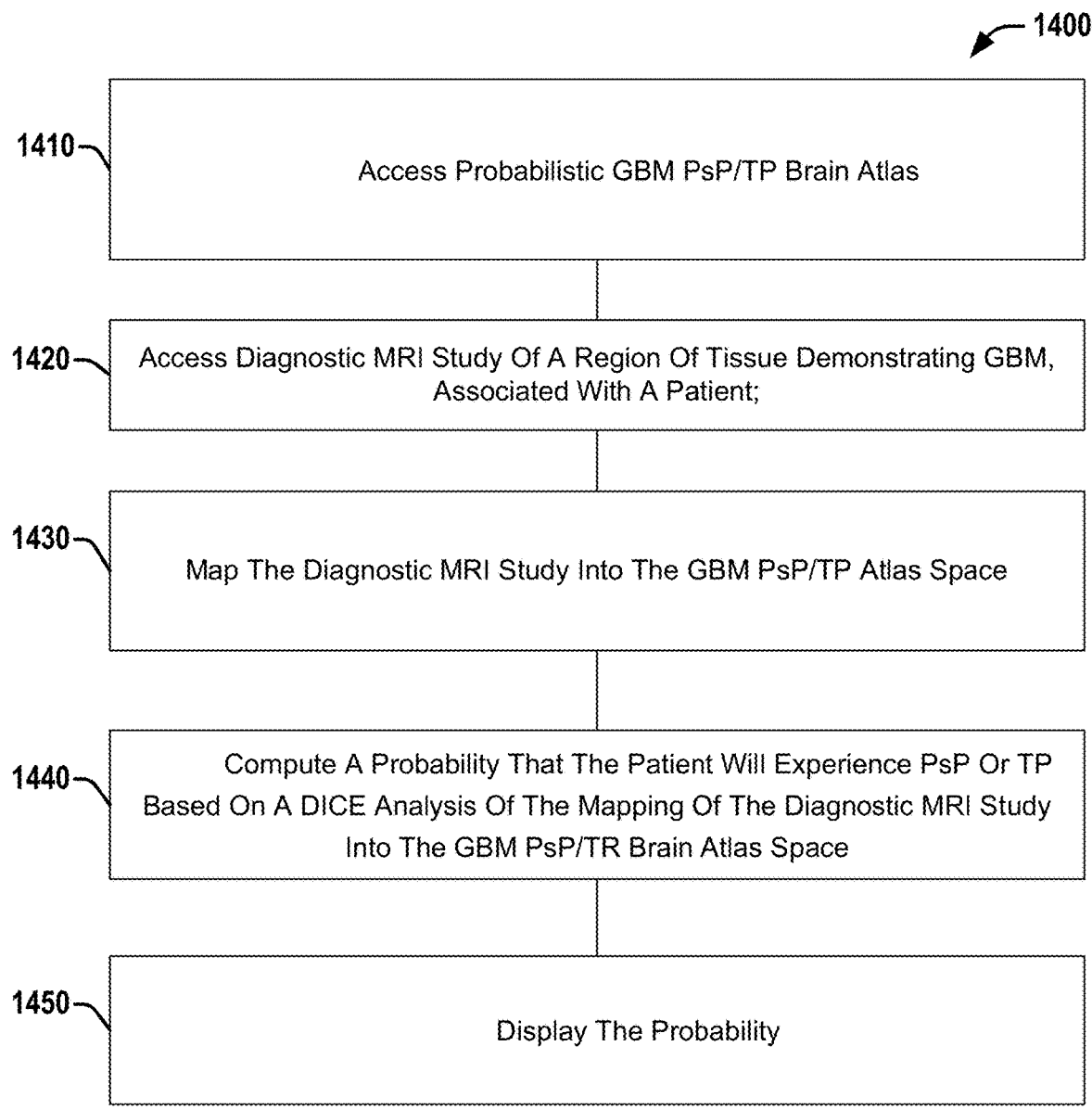
FIG. 14 illustrates a diagram of an example flow of a method or set of operations that computes a probability of TP versus PsP in a patient demonstrating GBM, according to various embodiments discussed herein

FIG. 14 illustrates a diagram of an example flow of a method or set of operations 1400 that computes a probability of TP versus PsP in a patient demonstrating GBM. Operations 1400 includes, at 1410, accessing a GBM PsP/TP brain atlas. The GBM PsP/TP brain atlas quantifies a frequency of occurrence of PsP in an enhancing lesion compartment and a peri-lesional hyperintensities compartment. The GBM PsP/TP brain atlas also quantifies a frequency of occurrence of TP in the enhancing lesion compartment and the peri-lesional hyperintensities compartment. The GBM PsP/TP brain atlas may be generated according to various embodiments described herein. Accessing the GBM PsP/TP brain atlas includes acquiring electronic data, reading from a computer file, receiving a computer file, reading from a computer memory, or other computerized activity not practically performed in the human mind.

Operations 1400 also includes, at 1420, accessing a diagnostic mpMRI study of a region of tissue demonstrating GBM. The diagnostic MRI study includes a representation of an enhancing lesion compartment and a peri-lesional hyperintensities compartment. The diagnostic MRI study is associated with a patient. Accessing the diagnostic mpMRI study includes acquiring electronic data, reading from a computer file, receiving a computer file, reading from a computer memory, or other computerized activity not practically performed in the human mind.

Operations 1400 also includes, at 1430, mapping the diagnostic mpMRI study into the GBM PsP/TP atlas space. In one embodiment, the diagnostic mpMRI study is mapped into the GBM PsP/TP atlas space using an affine registration technique. The segmented lesion of represented in the diagnostic mpMRI study is mapped to the PsP atlas and TP atlas, which facilitates obtaining a measure of overlap using DICE. Mapping the diagnostic mpMRI study includes acquiring electronic data, reading from a computer file, receiving a computer file, reading from a computer memory, or other computerized activity not practically performed in the human mind.

Operations 1400 also includes, at 1440, computing a probability that the patient will experience PsP or TP based on a DICE analysis of the mapping of the diagnostic mpMRI study into the GBM PsP/TP brain atlas space. Computing the probability includes acquiring electronic data, reading from a computer file, receiving a computer file, reading from a computer memory, or other computerized activity not practically performed in the human mind.

Operations 1400 further includes, at 1450, displaying the probability. Displaying the probability includes acquiring electronic data, reading from a computer file, receiving a computer file, reading from a computer memory, or other computerized activity not practically performed in the human mind.

In various embodiments, the probability may be computed using a machine learning classifier. For example, a machine learning classifier may be trained to distinguish a patient demonstrating GBM likely to experience PsP from a patient demonstrating GBM likely to experience TP based on a diagnostic mpMRI study associated with the patient. In this embodiment, training the machine learning classifier may include accessing a training dataset of mpMRI studies of patients demonstrating GBM. Each mpMRI study may include a plurality of MRI images (e.g., a Gd-T1w MRI image, a T2w MRI image, and a FLAIR MRI image) that can comprise a plurality of voxels, where each voxel can have an associated intensity. The training dataset can comprise both a positive training set of mpMRI studies and a negative training set of mpMRI studies in connection with a given medical condition (e.g., GBM). The positive training set can comprise mpMRI studies that have features (e.g., one or more features that have been determined to be predictively significant specifically in connection with the given medical condition, etc.) that are predictive of an outcome (e.g., TP, PsP) of the given medical condition (e.g., GBM). The negative training set can comprise images of samples that are irrelevant, have non-predictive patterns (e.g., non-lesion regions), have artifacts, or are non-diagnostic tissue.

Training the machine learning classifier may include accessing a training dataset of mpMRI studies of a patients demonstrating GBM, and a testing set of mpMRI studies of patients demonstrating GBM. The training dataset and the testing dataset of mpMRI studies are acquired from a population of patients that experienced pathologically proven GBM as described herein. Members of the population experienced either PsP or TP. Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining which features of members of the training dataset or testing dataset are most discriminative in distinguishing patients likely to experience TP from patients likely to experience PsP. Training the machine learning classifier may also include determining settings outside the classifier architecture but relevant to its learning behavior. Embodiments may further display operating parameters or characteristics of the machine learning classifier, during both training and testing, or during clinical operation.

Examples herein can include subject matter such as an apparatus, a personalized medicine system, a CADx system, an MRI system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating a quantitative population atlas of TP versus PsP in GBM, or the determination of a probability of a patient experiencing PsP or TP in GBM, according to embodiments and examples described herein.

Example 1 is a non-transitory computer-readable device storing computer-executable instructions that, when executed, cause a processor to perform operations, comprising: accessing a plurality of multi-parametric magnetic resonance imaging (mpMRI) studies associated with a plurality of patients demonstrating Glioblastoma (GBM), respectively, where at least one member of the plurality of mpMRI studies is associated with a patient that demonstrated pseudo-progression (PsP), and where at least one other, different member of the plurality of mpMRI studies is associated with a patient that demonstrated tumor progression (TP), where an mpMRI study includes a plurality of MRI images, where a member of the plurality of MRI images includes a plurality of associated voxels, a voxel having an intensity; generating a registered set of mpMRI studies by, for each member of the plurality of mpMRI studies, respectively: generating an enhancing lesion segmented image by segmenting an enhancing lesion compartment represented in a first MRI image acquired during a first MRI sequence of a member of the plurality of mpMRI studies associated with a patient; generating a peri-lesional hyperintensities segmented image by segmenting a peri-lesional hyperintensities compartment represented in a second, different MRI image acquired during a second, different MRI sequence of the member of the plurality of mpMRI studies associated with the patient; registering the enhancing lesion segmented image and the peri-lesional hyperintensities segmented image with a reference brain atlas; generating an enhancing lesion PsP population atlas by computing a voxel-wise frequency of occurrence of enhancing lesion of the members of the registered set of mpMRI studies associated with patients who demonstrated PsP; generating a peri-lesional hyperintensities PsP population atlas by computing a voxel-wise frequency of occurrence of peri-lesional hyperintensities of the members of the registered set of mpMRI studies associated with patients who demonstrated PsP; generating an enhancing lesion TP population atlas by computing a voxel-wise frequency of occurrence of enhancing lesion of the members of the registered set of mpMRI studies associated with patients who demonstrated TP; generating a peri-lesional hyperintensities TP population atlas by computing a voxel-wise frequency of occurrence of peri-lesional hyperintensities of members of the registered set of mpMRI studies who demonstrated TP; generating a frequency map for at least one of the enhancing lesion PsP population atlas, the peri-lesional hyperintensities PsP population atlas, the enhancing lesion TP population atlas, or the peri-lesional hyperintensities TP population atlas; and displaying the frequency map.

Example 2 comprises the subject matter of any variation of any of example 1, where the mpMRI study includes a Gd-T1w MRI image, a T2w MRI image, and a FLAIR MRI image, where the Gd-T1w MRI image, the T2w MRI image, and the FLAIR MRI image each includes a plurality of associated voxels, a voxel having an intensity.

Example 3 comprises the subject matter of any variation of any of example(s) 1-2, where generating the enhancing lesion segmented image includes segmenting an enhancing lesion compartment represented in the Gd-T1w MRI image; and generating the peri-lesional hyperintensities segmented image includes segmenting a peri-lesional hyperintensities compartment represented in the T2w MRI image, and segmenting a peri-lesional hyperintensities compartment represented in the FLAIR MRI image.

Example 4 comprises the subject matter of any variation of any of example(s) 1-3, where registering the enhancing lesion segmented image and the peri-lesional hyperintensities segmented image with a reference brain atlas comprises: generating a registered enhancing lesion segmented image and a registered peri-lesional hyperintensities segmented image by registering the enhancing lesion segmented image and the peri-lesional hyperintensities segmented image with the reference brain atlas using mutual information with twelve degrees of information; generating a registered, skull-stripped enhancing lesion segmented image and a registered, skull-stripped peri-lesional hyperintensities segmented image by skull stripping the registered enhancing lesion segmented image and the registered peri-lesional hyperintensities segmented image using a deformable surface classification approach; and bias field correcting the registered, skull-stripped enhancing lesion segmented image and the registered, skull-stripped peri-lesional hyperintensities segmented image using a nonparametric non-uniform intensity normalization technique.

Example 5 comprises the subject matter of any variation of any of example(s) 1-4, where computing the voxel-wise frequency of occurrence of enhancing lesion of the members of the registered set of mpMRI studies associated with patients who demonstrated PsP comprises computing the average intensity value for each voxel of each annotated enhancing lesion image of each mpMRI study associated with patients who demonstrated PsP; computing the voxel-wise frequency of occurrence of peri-lesional hyperintensities of the members of the registered set of mpMRI studies associated with patients who demonstrated PsP includes computing the average intensity value for each voxel of each annotated peri-lesional hyperintensities image of each multiparametric study associated with patients who demonstrated PsP; computing the voxel-wise frequency of occurrence of enhancing lesion of the members of the registered set of mpMRI studies associated with patients who demonstrated TP based on the registered set of mpMRI studies includes computing the average intensity value for each voxel of each annotated enhancing lesion image of each multiparametric study associated with patients who demonstrated TP; and computing the voxel-wise frequency of occurrence of peri-lesional hyperintensities of the members of the registered set of mpMRI studies associated with patients who demonstrated TP based on the registered set of mpMRI studies includes computing the average intensity value for each voxel of each annotated peri-lesional hyperintensities image of each multiparametric study associated with patients who demonstrated TP.

Example 6 comprises the subject matter of any variation of any of example(s) 1-5, the operations further comprising: accessing a diagnostic mpMRI study associated with a patient demonstrating GBM, where the diagnostic mpMRI study includes a plurality of MRI images, where a member of the plurality of MRI images includes a plurality of associated voxels, a voxel having an intensity; generating a registered diagnostic mpMRI study; computing a probability that the patient will experience TP or PsP based on a comparison of the registered diagnostic mpMRI study with the enhancing lesion PsP population atlas, the peri-lesional hyperintensities PsP population atlas, the enhancing lesion TP population atlas, and the peri-lesional hyperintensities TP population atlas; and displaying the probability.

Example 7 comprises the subject matter of any variation of any of example(s) 1-6, the operations further comprising: generating a personalized GBM treatment plan based, at least in part, on the probability; and optionally displaying the personalized GBM treatment plan.

Example 8 comprises the subject matter of any variation of any of example(s) 1-7, where generating the registered diagnostic mpMRI study comprises: generating a diagnostic enhancing lesion segmented image by segmenting an enhancing lesion compartment represented in the diagnostic mpMRI study associated with the patient; generating a diagnostic peri-lesional hyperintensities segmented image by segmenting a peri-lesional hyperintensities compartment represented in the diagnostic mpM RI study associated with the patient; registering the diagnostic enhancing lesion segmented image with the enhancing lesion PsP population atlas and the enhancing lesion TP population atlas; and registering the diagnostic peri-lesional hyperintensities segmented image with the peri-lesional hyperintensities PsP population atlas, and the peri-lesional hyperintensities TP population atlas.

Example 9 comprises the subject matter of any variation of any of example(s) 1-8, where computing the probability includes computing a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas.

Example 10 comprises the subject matter of any variation of any of example(s) 1-9, where the plurality of mpMRI studies is a plurality of post-treatment mpMRI studies, and where the diagnostic mpMRI study is a post-treatment mpMRI study; or where the plurality of mpMRI studies is a plurality of pre-treatment mpMRI studies, and where the diagnostic mpMRI study is a pre-treatment mpMRI study.

Example 11 comprises the subject matter of any variation of any of example(s) 1-10, the operations further comprising: generating an enhancing lesion compartment analysis of differential involvement (ADIFFI) map based on the enhancing lesion PsP population atlas and the enhancing lesion TP population atlas; generating a peri-lesional hyperintensities compartment ADIFFI map based on the peri-lesional hyperintensities PsP population atlas and the peri-lesional hyperintensities TP population atlas; and displaying the enhancing lesion compartment ADIFFI map or the peri-lesional hyperintensities compartment ADIFFI map.

Example 12 comprises the subject matter of any variation of any of example(s) 1-11, the operations further comprising: identifying anatomic areas of localization of TP or PsP by partitioning the enhancing lesion compartment ADIFFI map or the peri-lesional hyperintensities compartment ADIFFI map using pre-labelled anatomical structures in the reference brain atlas space; and displaying the identified anatomic areas of localization of TP or PsP.

Example 13 comprises the subject matter of any variation of any of example(s) 1-12, the operations further comprising: generating a cluster-size corrected enhancing lesion compartment ADIFFI map by performing a cluster-size correction of the enhancing lesion compartment ADIFFI map; generating a cluster-size corrected peri-lesional hyperintensities compartment ADIFFI map by performing a cluster-size correction of the peri-lesional hyperintensities compartment ADIFFI map; and displaying the cluster-size corrected enhancing lesion compartment ADIFFI map or the cluster-size corrected peri-lesional hyperintensities compartment ADIFFI map.

Example 14 comprises the subject matter of any variation of any of example(s) 1-13, where the reference brain atlas is a Montreal Neurological Institute (MNI) MNI152 atlas.

Example 15 comprises an apparatus that facilitates generation of a quantitative population atlas of tumor progression (TP) versus pseudo-progression (PsP) in Glioblastoma (GBM), the apparatus comprising: a processor; a memory configured to store a multi-parametric magnetic resonance imaging (mpMRI) study associated with a patient demonstrating GBM, where the mpMRI study includes a plurality of MRI images, where an MRI image includes a plurality of voxels, wherein each voxel of the plurality of voxels has an associated intensity; an input/output (I/O) interface; a set of circuits; and an interface that connects the processor, the memory, the I/O interface, and the set of circuits, the set of circuits comprising: an image acquisition circuit configured to access a plurality of mpMRI studies associated with a plurality of patients demonstrating GBM, respectively, where at least one member of the mpMRI studies is associated with a patient that demonstrated PsP, and where at least one other, different member of the plurality of mpMRI studies is associated with a patient that demonstrated TP; a segmentation and registration circuit configured to: generate a registered set of mpMRI studies by, for each member of the plurality of mpMRI studies, respectively: generating an enhancing lesion segmented image by segmenting an enhancing lesion compartment represented in a first MRI image acquired during a first MRI sequence of a member of the plurality of mpMRI studies associated with a patient; generating a peri-lesional hyperintensities segmented image by segmenting a peri-lesional hyperintensities compartment represented in a second, different MRI image acquired during a second, different MRI sequence of the member of the plurality of mpMRI studies associated with the patient; and registering the enhancing lesion segmented image and the peri-lesional hyperintensities segmented image with a reference brain atlas; an atlas generation circuit configured to: generate an enhancing lesion PsP population atlas by computing a voxel-wise frequency of occurrence of enhancing lesion of the members of the registered set of mpMRI studies associated with patients who demonstrated PsP; generate a peri-lesional hyperintensities PsP population atlas by computing a voxel-wise frequency of occurrence of peri-lesional hyperintensities of the members of the registered set of mpMRI studies associated with patients who demonstrated PsP; generate an enhancing lesion TP population atlas by computing a voxel-wise frequency of occurrence of enhancing lesion of the members of the registered set of mpMRI studies associated with patients who demonstrated TP; and generate a peri-lesional hyperintensities TP population atlas by computing a voxel-wise frequency of occurrence of peri-lesional hyperintensities of members of the registered set of mpMRI studies who demonstrated TP; and a display circuit configured to: generate a frequency map for at least one of the enhancing lesion PsP population atlas, the peri-lesional hyperintensities PsP population atlas, the enhancing lesion TP population atlas, or the peri-lesional hyperintensities TP population atlas; and display the frequency map.

Example 16 comprises the subject matter of any variation of example 15, where the mpMRI study includes a Gd-T1w MRI image, a T2w MRI image, and a FLAIR MRI image, where the Gd-T1w MRI image, the T2w MRI image, and the FLAIR MRI image each includes a plurality of associated voxels, a voxel having an intensity; and where the segmentation and registration circuit is configured to: generate the enhancing lesion segmented image by segmenting an enhancing lesion compartment represented in the Gd-T1w MRI image; and generate the peri-lesional hyperintensities segmented image by segmenting a peri-lesional hyperintensities compartment represented in the T2w MRI image, and segmenting a peri-lesional hyperintensities compartment represented in the FLAIR MRI image.

Example 17 comprises the subject matter of any variation of any of example(s) 15-16, where the atlas generation circuit is configured to: compute the voxel-wise frequency of occurrence of enhancing lesion of the members of the registered set of mpMRI studies associated with patients who demonstrated PsP by computing the average intensity value for each voxel of each annotated enhancing lesion image of each mpMRI study, respectively, associated with patients who demonstrated PsP; compute the voxel-wise frequency of occurrence of peri-lesional hyperintensities of the members of the registered set of multi-parametric MRI studies associated with patients who demonstrated PsP by computing the average intensity value for each voxel of each annotated peri-lesional hyperintensities image of each mpMRI study, respectively, associated with patients who demonstrated PsP; compute the voxel-wise frequency of occurrence of enhancing lesion of the members of the registered set of mpMRI studies associated with patients who demonstrated TP based on the registered set of mpMRI studies by computing the average intensity value for each voxel of each annotated enhancing lesion image of each mpMRI study, respectively, associated with patients who demonstrated TP; and compute the voxel-wise frequency of occurrence of peri-lesional hyperintensities of the members of the registered set of mpMRI studies associated with patients who demonstrated TP based on the registered set of mpMRI studies by computing the average intensity value for each voxel of each annotated peri-lesional hyperintensities image of each multiparametric study associated with patients who demonstrated TP.

Example 18 comprises the subject matter of any variation of any of example(s) 15-17, the set of circuits further comprising a PsP/TP prediction circuit configured to: access a diagnostic mpMRI study associated with a patient demonstrating GBM, where the diagnostic mpMRI study includes a plurality of MRI images, where a member of the plurality of MRI images includes a plurality of associated voxels, a voxel having an intensity; generate a registered diagnostic mpMRI study based on the diagnostic mpMRI study by: generating a diagnostic enhancing lesion segmented image by segmenting an enhancing lesion compartment represented in the diagnostic mpMRI study associated with the patient; generating a diagnostic peri-lesional hyperintensities segmented image by segmenting a peri-lesional hyperintensities compartment represented in the diagnostic mpMRI study associated with the patient; registering the diagnostic enhancing lesion segmented image with the enhancing lesion PsP population atlas and the enhancing lesion TP population atlas; and registering the diagnostic peri-lesional hyperintensities segmented image with the peri-lesional hyperintensities PsP population atlas, and the peri-lesional hyperintensities TP population atlas; and compute a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas; and compute a probability that the patient will experience TP or PsP based on a DICE score; and where the display circuit is further configured to optionally display the probability or the DICE score.

Example 19 comprises the subject matter of any variation of any of example(s) 15-18, the set of circuits further comprising a personalized GBM treatment plan circuit configured to: generate a personalized GBM treatment plan based, at least in part, on the probability; and where the display circuit is further configured to optionally display the personalized GBM treatment plan.

Example 20 is a non-transitory computer-readable medium storing computer-executable instructions that, when executed, cause a processor to perform operations, comprising: accessing a GBM PsP/TP brain atlas, where the GBM PsP/TP brain atlas quantifies a frequency of occurrence of PsP in an enhancing lesion compartment and a peri-lesional hyperintensities compartment, and quantifies a frequency of occurrence of TP in the enhancing lesion compartment and the peri-lesional hyperintensities compartment; accessing a diagnostic multi-parametric MRI (mpMRI) study of a region of tissue demonstrating GBM, where the diagnostic mpMRI study includes a representation of an enhancing lesion compartment and a peri-lesional hyperintensities compartment, where the diagnostic mpMRI study is associated with a patient; mapping the diagnostic mpMRI study into the GBM PsP/TP atlas space; computing a probability that the patient will experience PsP or TP based on a DICE analysis of the mapping of the diagnostic mpMRI study into the GBM PsP/TP brain atlas space; and displaying the probability.

Example 21 comprises an apparatus comprising means for executing any of the described operations of examples 1-20.

Example 22 comprises a machine readable medium that stores instructions for execution by a processor to perform any of the described operations of examples 1-20.

Example 23 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that, when executed, cause a processor to perform operations, the operations comprising:
    accessing a plurality of multi-parametric magnetic resonance imaging (mpMRI) studies associated with a plurality of patients demonstrating Glioblastoma (GBM), respectively, where at least one member of the plurality of mpMRI studies is associated with a patient that demonstrated pseudo-progression (PsP), and where at least one other, different member of the plurality of mpMRI studies is associated with a patient that demonstrated tumor progression (TP), where an mpMRI study includes a plurality of MRI images, where a member of the plurality of MRI images includes a plurality of associated voxels, a voxel having an intensity;
    generating a registered set of mpMRI studies by, for each member of the plurality of mpMRI studies, respectively:
        generating an enhancing lesion segmented image by segmenting an enhancing lesion compartment represented in a first MRI image acquired during a first MRI sequence of a member of the plurality of mpMRI studies associated with a patient;
        generating a peri-lesional hyperintensities segmented image by segmenting a peri-lesional hyperintensities compartment represented in a second, different MRI image acquired during a second, different MRI sequence of the member of the plurality of mpMRI studies associated with the patient;
        registering the enhancing lesion segmented image and the peri-lesional hyperintensities segmented image with a reference brain atlas;
    generating an enhancing lesion PsP population atlas by computing a voxel-wise frequency of occurrence of enhancing lesion of the members of the registered set of mpMRI studies associated with patients who demonstrated PsP;
    generating a peri-lesional hyperintensities PsP population atlas by computing a voxel-wise frequency of occurrence of peri-lesional hyperintensities of the members of the registered set of mpMRI studies associated with patients who demonstrated PsP;
    generating an enhancing lesion TP population atlas by computing a voxel-wise frequency of occurrence of enhancing lesion of the members of the registered set of mpMRI studies associated with patients who demonstrated TP;
    generating a peri-lesional hyperintensities TP population atlas by computing a voxel-wise frequency of occurrence of peri-lesional hyperintensities of members of the registered set of mpMRI studies who demonstrated TP;
    generating a frequency map for at least one of the enhancing lesion PsP population atlas, the peri-lesional hyperintensities PsP population atlas, the enhancing lesion TP population atlas, or the peri-lesional hyperintensities TP population atlas; and
    displaying the frequency map.

2. The non-transitory computer-readable storage device of claim 1, where the mpMRI study includes a Gd-T1w MRI image, a T2w MRI image, and a FLAIR MRI image, where the Gd-T1w MRI image, the T2w MRI image, and the FLAIR MRI image each includes a plurality of associated voxels, a voxel having an intensity.

3. The non-transitory computer-readable storage device of claim 2, where generating the enhancing lesion segmented image includes segmenting an enhancing lesion compartment represented in the Gd-T1w MRI image; and
    generating the peri-lesional hyperintensities segmented image includes segmenting a peri-lesional hyperintensities compartment represented in the T2w MRI image, and segmenting a peri-lesional hyperintensities compartment represented in the FLAIR MRI image.

4. The non-transitory computer-readable storage device of claim 1, where registering the enhancing lesion segmented image and the peri-lesional hyperintensities segmented image with a reference brain atlas comprises:
    generating a registered enhancing lesion segmented image and a registered peri-lesional hyperintensities segmented image by registering the enhancing lesion segmented image and the peri-lesional hyperintensities segmented image with the reference brain atlas using mutual information with twelve degrees of information;
    generating a registered, skull-stripped enhancing lesion segmented image and a registered, skull-stripped peri-lesional hyperintensities segmented image by skull stripping the registered enhancing lesion segmented image and the registered peri-lesional hyperintensities segmented image using a deformable surface classification approach; and
    bias field correcting the registered, skull-stripped enhancing lesion segmented image and the registered, skull-stripped peri-lesional hyperintensities segmented image using a nonparametric non-uniform intensity normalization technique.

5. The non-transitory computer-readable storage device of claim 1 where:
    computing the voxel-wise frequency of occurrence of enhancing lesion of the members of the registered set of mpMRI studies associated with patients who demonstrated PsP comprises computing the average intensity value for each voxel of each annotated enhancing lesion image of each mpMRI study associated with patients who demonstrated PsP;

computing the voxel-wise frequency of occurrence of peri-lesional hyperintensities of the members of the registered set of mpMRI studies associated with patients who demonstrated PsP includes computing the average intensity value for each voxel of each annotated peri-lesional hyperintensities image of each multiparametric study associated with patients who demonstrated PsP;

computing the voxel-wise frequency of occurrence of enhancing lesion of the members of the registered set of mpMRI studies associated with patients who demonstrated TP based on the registered set of mpMRI studies includes computing the average intensity value for each voxel of each annotated enhancing lesion image of each multiparametric study associated with patients who demonstrated TP; and computing the voxel-wise frequency of occurrence of peri-lesional hyperintensities of the members of the registered set of mpMRI studies associated with patients who demonstrated TP based on the registered set of mpMRI studies includes computing the average intensity value for each voxel of each annotated peri-lesional hyperintensities image of each multiparametric study associated with patients who demonstrated TP.

6. The non-transitory computer-readable storage device of claim 1, the operations further comprising:

accessing a diagnostic mpMRI study associated with a patient demonstrating GBM, where the diagnostic mpMRI study includes a plurality of MRI images, where a member of the plurality of MRI images includes a plurality of associated voxels, a voxel having an intensity;

generating a registered diagnostic mpMRI study;

computing a probability that the patient will experience TP or PsP based on a comparison of the registered diagnostic mpMRI study with the enhancing lesion PsP population atlas, the peri-lesional hyperintensities PsP population atlas, the enhancing lesion TP population atlas, and the peri-lesional hyperintensities TP population atlas; and displaying the probability.

7. The non-transitory computer-readable storage device of claim 6, the operations further comprising:

generating a personalized GBM treatment plan based, at least in part, on the probability; and optionally displaying the personalized GBM treatment plan.

8. The non-transitory computer-readable storage device of claim 6, where generating the registered diagnostic mpMRI study comprises:

generating a diagnostic enhancing lesion segmented image by segmenting an enhancing lesion compartment represented in the diagnostic mpMRI study associated with the patient;

generating a diagnostic peri-lesional hyperintensities segmented image by segmenting a peri-lesional hyperintensities compartment represented in the diagnostic mpMRI study associated with the patient;

registering the diagnostic enhancing lesion segmented image with the enhancing lesion PsP population atlas and the enhancing lesion TP population atlas; and registering the diagnostic peri-lesional hyperintensities segmented image with the peri-lesional hyperintensities PsP population atlas, and the peri-lesional hyperintensities TP population atlas.

9. The non-transitory computer-readable storage device of claim 8, where computing the probability includes computing a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas.

10. The non-transitory computer-readable storage device of claim 6, where the plurality of mpMRI studies is a plurality of post-treatment mpMRI studies, and where the diagnostic mpMRI study is a post-treatment mpMRI study; or where the plurality of mpMRI studies is a plurality of pre-treatment mpMRI studies, and where the diagnostic mpMRI study is a pre-treatment mpMRI study.

11. The non-transitory computer-readable storage device of claim 10, the operations further comprising:

generating a cluster-size corrected enhancing lesion compartment ADIFFI map by performing a cluster-size correction of the enhancing lesion compartment ADIFFI map;

generating a cluster-size corrected peri-lesional hyperintensities compartment ADIFFI map by performing a cluster-size correction of the peri-lesional hyperintensities compartment ADIFFI map; and displaying the cluster-size corrected enhancing lesion compartment ADIFFI map or the cluster-size corrected peri-lesional hyperintensities compartment ADIFFI map.

12. The non-transitory computer-readable storage device of claim 1, the operations further comprising:

generating an enhancing lesion compartment analysis of differential involvement (ADIFFI) map based on the enhancing lesion PsP population atlas and the enhancing lesion TP population atlas;

generating a peri-lesional hyperintensities compartment ADIFFI map based on the peri-lesional hyperintensities PsP population atlas and the peri-lesional hyperintensities TP population atlas; and displaying the enhancing lesion compartment ADIFFI map or the peri-lesional hyperintensities compartment ADIFFI map.

13. The non-transitory computer-readable storage device of claim 12, the operations further comprising:

identifying anatomic areas of localization of TP or PsP by partitioning the enhancing lesion compartment ADIFFI map or the peri-lesional hyperintensities compartment ADIFFI map using pre-labelled anatomical structures in the reference brain atlas space; and displaying the identified anatomic areas of localization of TP or PsP.

14. The non-transitory computer-readable storage device of claim 1, where the reference brain atlas is a Montreal Neurological Institute (MNI) MNI152 atlas.

15. An apparatus that facilitates generation of a quantitative population atlas of tumor progression (TP) versus pseudo-progression (PsP) in Glioblastoma (GBM), the apparatus comprising:

a processor;

a memory configured to store a multi-parametric magnetic resonance imaging (mpMRI) study associated with a patient demonstrating GBM, where the mpMRI study includes a plurality of MRI images, where an MRI image includes a plurality of voxels, wherein each voxel of the plurality of voxels has an associated intensity;
an input/output (I/O) interface;
a set of circuits; and
an interface that connects the processor, the memory, the I/O interface, and the set of circuits, the set of circuits comprising:
an image acquisition circuit configured to access a plurality of mpMRI studies associated with a plurality of patients demonstrating GBM, respectively, where at least one member of the mpMRI studies is associated with a patient that demonstrated PsP, and where at least one other, different member of the plurality of mpMRI studies is associated with a patient that demonstrated TP;
a segmentation and registration circuit configured to:
generate a registered set of mpMRI studies by, for each member of the plurality of mpMRI studies, respectively:
generating an enhancing lesion segmented image by segmenting an enhancing lesion compartment represented in a first MRI image acquired during a first MRI sequence of a member of the plurality of mpMRI studies associated with a patient;
generating a peri-lesional hyperintensities segmented image by segmenting a peri-lesional hyperintensities compartment represented in a second, different MRI image acquired during a second, different MRI sequence of the member of the plurality of mpMRI studies associated with the patient; and
registering the enhancing lesion segmented image and the peri-lesional hyperintensities segmented image with a reference brain atlas;
an atlas generation circuit configured to:
generate an enhancing lesion PsP population atlas by computing a voxel-wise frequency of occurrence of enhancing lesion of the members of the registered set of mpMRI studies associated with patients who demonstrated PsP;
generate a peri-lesional hyperintensities PsP population atlas by computing a voxel-wise frequency of occurrence of peri-lesional hyperintensities of the members of the registered set of mpMRI studies associated with patients who demonstrated PsP;
generate an enhancing lesion TP population atlas by computing a voxel-wise frequency of occurrence of enhancing lesion of the members of the registered set of mpMRI studies associated with patients who demonstrated TP; and
generate a peri-lesional hyperintensities TP population atlas by computing a voxel-wise frequency of occurrence of peri-lesional hyperintensities of members of the registered set of mpMRI studies who demonstrated TP; and
a display circuit configured to:
generate a frequency map for at least one of the enhancing lesion PsP population atlas, the peri-lesional hyperintensities PsP population atlas, the enhancing lesion TP population atlas, or the peri-lesional hyperintensities TP population atlas; and display the frequency map.

16. The apparatus of claim 15, where the mpMRI study includes a Gd-T1w MRI image, a T2w MRI image, and a FLAIR MRI image, where the Gd-T1w MRI image, the T2w MRI image, and the FLAIR MRI image each includes a plurality of associated voxels, a voxel having an intensity; and
where the segmentation and registration circuit is configured to:
generate the enhancing lesion segmented image by segmenting an enhancing lesion compartment represented in the Gd-T1w MRI image; and
generate the peri-lesional hyperintensities segmented image by segmenting a peri-lesional hyperintensities compartment represented in the T2w MRI image, and segmenting a peri-lesional hyperintensities compartment represented in the FLAIR MRI image.

17. The apparatus of claim 15, where the atlas generation circuit is configured to:
compute the voxel-wise frequency of occurrence of enhancing lesion of the members of the registered set of mpMRI studies associated with patients who demonstrated PsP by computing the average intensity value for each voxel of each annotated enhancing lesion image of each mpMRI study, respectively, associated with patients who demonstrated PsP;
compute the voxel-wise frequency of occurrence of peri-lesional hyperintensities of the members of the registered set of multi-parametric MRI studies associated with patients who demonstrated PsP by computing the average intensity value for each voxel of each annotated peri-lesional hyperintensities image of each mpMRI study, respectively, associated with patients who demonstrated PsP;
compute the voxel-wise frequency of occurrence of enhancing lesion of the members of the registered set of mpMRI studies associated with patients who demonstrated TP based on the registered set of mpMRI studies by computing the average intensity value for each voxel of each annotated enhancing lesion image of each mpMRI study, respectively, associated with patients who demonstrated TP; and
compute the voxel-wise frequency of occurrence of peri-lesional hyperintensities of the members of the registered set of mpMRI studies associated with patients who demonstrated TP based on the registered set of mpMRI studies by computing the average intensity value for each voxel of each annotated peri-lesional hyperintensities image of each multiparametric study associated with patients who demonstrated TP.

18. The apparatus of claim 15, the set of circuits further comprising a PsP/TP prediction circuit configured to:
access a diagnostic mpMRI study associated with a patient demonstrating GBM, where the diagnostic mpMRI study includes a plurality of MRI images, where a member of the plurality of MRI images includes a plurality of associated voxels, a voxel having an intensity;
generate a registered diagnostic mpMRI study based on the diagnostic mpMRI study by:
generating a diagnostic enhancing lesion segmented image by segmenting an enhancing lesion compartment represented in the diagnostic mpMRI study associated with the patient;
generating a diagnostic peri-lesional hyperintensities segmented image by segmenting a peri-lesional hyperintensities compartment represented in the diagnostic mpMRI study associated with the patient;
registering the diagnostic enhancing lesion segmented image with the enhancing lesion PsP population atlas and the enhancing lesion TP population atlas; and registering the diagnostic peri-lesional hyperintensities segmented image with the peri-lesional hyperintensities PsP population atlas, and the peri-lesional hyperintensities TP population atlas; and compute a DICE score based on a comparison of the registered diagnostic enhancing lesion segmented image and the registered diagnostic peri-lesional hyperintensities segmented image with the enhancing lesion PsP population atlas, the peri-lesional hyperintensities PsP population atlas, the enhancing lesion TP population atlas, and the peri-lesional hyperintensities TP population atlas; and compute a probability that the patient will experience TP or PsP based on a DICE score; and where the display circuit is further configured to optionally display the probability or the DICE score.

19. The apparatus of claim 18, the set of circuits further comprising a personalized GBM treatment plan circuit configured to:

generate a personalized GBM treatment plan based, at least in part, on the probability; and where the display circuit is further configured to optionally display the personalized GBM treatment plan.

\* \* \* \* \*